United States Patent
Olinski et al.

(10) Patent No.: US 9,441,215 B2
(45) Date of Patent: Sep. 13, 2016

(54) POLYPEPTIDES HAVING PROTEASE ACTIVITY

(71) Applicant: Novozymes A/S, Bagsvaerd (DK)

(72) Inventors: Robert Piotr Olinski, Vaerloese (DK); Peter Rahbek Oestergaard, Virum (DK); Katrine Pontoppidan Fruergaard, Lynge (DK); Tine Hoff, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/655,495

(22) PCT Filed: Feb. 5, 2014

(86) PCT No.: PCT/EP2014/052218
§ 371 (c)(1),
(2) Date: Jun. 25, 2015

(87) PCT Pub. No.: WO2014/122161
PCT Pub. Date: Aug. 14, 2014

(65) Prior Publication Data
US 2015/0344860 A1 Dec. 3, 2015

Related U.S. Application Data

(60) Provisional application No. 61/763,518, filed on Feb. 12, 2013.

(30) Foreign Application Priority Data

Feb. 6, 2013 (EP) ..................................... 13154179

(51) Int. Cl.
*C12N 9/48* (2006.01)
*C12N 15/00* (2006.01)
*C12N 9/52* (2006.01)

(52) U.S. Cl.
CPC ................. *C12N 9/52* (2013.01); *A23K 10/14* (2016.05); *A23K 20/147* (2016.05); *A23K 20/174* (2016.05); *A23K 20/189* (2016.05); *A23K 20/20* (2016.05); *A23K 50/30* (2016.05); *A23K 50/75* (2016.05); *A23K 50/80* (2016.05)

(58) Field of Classification Search
CPC ................................ C12N 9/48; C12N 15/00
See application file for complete search history.

(56) References Cited

U.S. PATENT DOCUMENTS

| | | | |
|---|---|---|---|
| 2,653,899 | A | 9/1953 | Bunch et al. |
| 8,535,927 | B1 | 9/2013 | Jones et al. |
| 2008/0004186 | A1 | 1/2008 | Estell et al. |
| 2009/0111161 | A1 | 4/2009 | Jones et al. |
| 2010/0095987 | A1 | 4/2010 | Jones et al. |
| 2011/0081711 | A1 | 4/2011 | Jones et al. |

FOREIGN PATENT DOCUMENTS

| | | |
|---|---|---|
| WO | 95/28850 A1 | 11/1995 |
| WO | 01/58275 A2 | 8/2001 |
| WO | 01/58276 A2 | 8/2001 |
| WO | 02/052948 A2 | 7/2002 |
| WO | 2004/034776 A2 | 4/2004 |
| WO | 2004/072221 A2 | 8/2004 |
| WO | 2004/072279 A2 | 8/2004 |
| WO | 2004/077960 A1 | 9/2004 |
| WO | 2004/111220 A1 | 12/2004 |
| WO | 2004/111223 A1 | 12/2004 |
| WO | 2005/035747 A1 | 4/2005 |
| WO | 2005/052161 A2 | 6/2005 |
| WO | 2005/123911 A2 | 12/2005 |
| WO | 2008/002472 A2 | 1/2008 |
| WO | 2008/042392 A1 | 4/2008 |
| WO | 2008/048392 A1 | 4/2008 |
| WO | 2008/153925 A2 | 12/2008 |
| WO | 2008/153934 A2 | 12/2008 |
| WO | 2009/058679 A1 | 5/2009 |
| WO | 2013/110766 A1 | 8/2013 |

OTHER PUBLICATIONS

Csepregi et al., UniProt Accession No. H0K7C (2012).
Jani et al., Bulletin of Environment, Pharmacology and Life Sciences, vol. 1, No. 6, pp. 84-92 (2012).
Jones et al., Geneseq Accession No. AEA80317 (2005).
Jones et al., Geneseq Accession No. AWA8820 (2005).
Klenk et al., UniProt Accession No. H8GAL4 (2012).
Lucas et al., UniProt Accession No. D2PRB9 (2010).
Lucas et al., UniProt Accession No. G4IXC2 (2011).
Lucas et al., UniProt Accession No. G4J6Q2 (2011).
Lucas et al., UniProt Accession No. H1JPF3 (2012).
Lucas et al., UniProt Accession No. H5XEH4 (2012).
Lucas et al., UniProt Accession No. I0V8H8 (2012).
Olinski et al., Geneseq Accession No. BAR72286 (2013).
Oliynyk et al., EMBL Accession No. AM420293 (2007).
Oliynyk et al., Nature Biotechnology, vol. 25, pp. 447-453 (2007).
Oliynyk et al., UniProt Accession No. A4F726 (2007).
Oliynyk et al., UniProt Accession No. A4FNQ0 (2007).
Pati et al., GenBank Accession No. CP001683 (2009).
Pati et al., Standards in Genomic Sciences, vol. 1, No. 2, pp. 141-149 (2009).
Pati et al., UniProt Accession No. C7MV18 (2009).
Pati et al., EMBL Accession No. ACU9697 (2011).
Strobel et al., UniProt Accession No. K0JQQ4 (2012).
Strobel et al., UniProt Accession No. K0JWC2 (2012).
Yum et al., Biosci. Biotech. Biochem., vol. 58, No. 3, pp. 470-474 (1994).
Yum et al., UniProt Accession No. Q55353 (1996).
Strobel et al., BMC Genomics, vol. 13, No. 465, pp. 1-13 (2012).

*Primary Examiner* — Maryam Monshipouri
(74) *Attorney, Agent, or Firm* — Elias Lambiris

(57) ABSTRACT

The present invention relates to isolated polypeptides having protease activity, and the use of isolated polypeptides having protease activity in animal feed. It also relates to the use of isolated nucleic acid sequences encoding the proteases in the recombinant production of isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, particularly using the proteases in animal feed.

20 Claims, 3 Drawing Sheets

```
                        SEQUENCE LISTING

<160> NUMBER OF SEQ ID NOS: 14

<210> SEQ ID NO 1
<211> LENGTH: 1334
<212> TYPE: DNA
<213> ORGANISM: Saccharopolyspora erythraea
<220> FEATURE:
<221> NAME/KEY: CDS
<222> LOCATION: (101)..(1231)
<220> FEATURE:
<221> NAME/KEY: sig_peptide
<222> LOCATION: (101)..(223)
<220> FEATURE:
<221> NAME/KEY: mat_peptide
<222> LOCATION: (683)..(1231)

<400> SEQUENCE: 1
cggtgagata tgcgtcaaaa gatggatgtg cacgacttgt cctcgccgaa tacttgttcg        60
ccgacggggg tccggtaacg cggaacaagg gagacagcac atg aag cgc aga ctt       115
                                             Met Lys Arg Arg Leu
                                                             -190 gcg gcc cgg gtg acg ggg tcc gtg att ttc gcg gct ggc acg atc            160
Ala Ala Arg Val Thr Gly Ser Val Ile Phe Ala Ala Gly Thr Ile
                -185             -180                 -175 gcc gcc ctg acc gtg ccc gcc acg gcg aat ccg acc gcg ccc gcg            205
Ala Ala Leu Thr Val Pro Ala Thr Ala Asn Pro Thr Ala Pro Ala
                -170             -165                 -160 ccg gtc gcc gcg gag gcc gcg acc ctg atg gag gcg atg cag cgc            250
Pro Val Ala Ala Glu Ala Ala Thr Leu Met Glu Ala Met Gln Arg
                -155             -150                 -145 gac ctg ggc ctg acc gcc gag cag gcc gct gag cgc ctc gcc gac            295
Asp Leu Gly Leu Thr Ala Glu Gln Ala Ala Glu Arg Leu Ala Asp
                -140             -135                 -130 gag gcc gct gcc acc cgc gcc gac cag agc ctg cgc ggc acc ctc            340
```

```
                Glu Ala Ala Ala Thr Arg Ala Asp Gln Ser Leu Arg Gly Thr Leu
                                -125                -120                -115 ggc tcc gcg ttc ggc ggc tcc cac tac gac gcc gcg ctc ggc aag        385
Gly Ser Ala Phe Gly Gly Ser His Tyr Asp Ala Ala Leu Gly Lys
            -110                -105                -100 ctc gtc gtc ggc gtg acc gac gcc ggc ctc ctc gac gag gtc cgc gcc    433
Leu Val Val Gly Val Thr Asp Ala Gly Leu Leu Asp Glu Val Arg Ala
        -95                 -90                 -85 gcc ggg gcc gac ggc gag ctg gtc cag cac aac gtc cag cag ctc gac    481
Ala Gly Ala Asp Gly Glu Leu Val Gln His Asn Val Gln Gln Leu Asp
            -80                 -75                 -70 ggc gtc gcc gac ggc ctc gac gcg cag tcc gcg cgc gcc ccg cag tcg    529
Gly Val Ala Asp Gly Leu Asp Ala Gln Ser Ala Arg Ala Pro Gln Ser
        -65                 -60                 -55 gtc acc ggc tgg tac gtg gac tcc agc agc aac tcc gtg gtc ctg acc    577
Val Thr Gly Trp Tyr Val Asp Ser Ser Ser Asn Ser Val Val Leu Thr
            -50                 -45                 -40 acc gcc ccg ggc aca gcc ggg cag gcg acc gac ttc gtc cgc gcc agc    625
Thr Ala Pro Gly Thr Ala Gly Gln Ala Thr Asp Phe Val Arg Ala Ser
-35                 -30                 -25                 -20 ggg gtg gac gcc ggc gcc gtg cgc gtc gtc gag tcc gcc gag cag ccc    673
Gly Val Asp Ala Gly Ala Val Arg Val Val Glu Ser Ala Glu Gln Pro
            -15                 -10                 -5 cgg acc tac gcc gac gtc atc ggc ggc gac gcc tac tac atc ggc agc    721
Arg Thr Tyr Ala Asp Val Ile Gly Gly Asp Ala Tyr Tyr Ile Gly Ser
        -1  1                   5                   10 ggt tcc cgc tgc tcg gtc ggc ttc tcc gtg cag ggc ggc ttc gtg acc    769
Gly Ser Arg Cys Ser Val Gly Phe Ser Val Gln Gly Gly Phe Val Thr
            15                  20                  25 gcg ggc cac tgc ggc aac cag ggc gac agc acc agc cag ccg agc ggc    817
Ala Gly His Cys Gly Asn Gln Gly Asp Ser Thr Ser Gln Pro Ser Gly
30                  35                  40                  45 acc ttc gag ggc tcg tcc ttc ccg ggc aac gac tac ggc tgg gtc cgg    865
Thr Phe Glu Gly Ser Ser Phe Pro Gly Asn Asp Tyr Gly Trp Val Arg
            50                  55                  60 acc gct tcc ggc gag aac ccg gtt ccg ctg gtc aac gac tac cag ggc    913
Thr Ala Ser Gly Glu Asn Pro Val Pro Leu Val Asn Asp Tyr Gln Gly
        65                  70                  75 ggc acc gtc ggc gtc gcc ggc tcc agc gag gcc gcc gag ggc gcg tcg    961
Gly Thr Val Gly Val Ala Gly Ser Ser Glu Ala Ala Glu Gly Ala Ser
            80                  85                  90 atc tgc cgt tcc ggc tcc acg acc ggc tgg cac tgc ggc acc gtc gag    1009
Ile Cys Arg Ser Gly Ser Thr Thr Gly Trp His Cys Gly Thr Val Glu
        95                  100                 105 gca aag aac cag acg gtg cgc tac ccg cag ggc acc gtc gag ggc ctg    1057
Ala Lys Asn Gln Thr Val Arg Tyr Pro Gln Gly Thr Val Glu Gly Leu
110                 115                 120                 125 acc cgc acc aac gtg tgc gcc gag ccc ggt gac tcc ggc ggt cg tgg    1105
Thr Arg Thr Asn Val Cys Ala Glu Pro Gly Asp Ser Gly Gly Ser Trp
            130                 135                 140 ctg tcc ggc gac cag gcc cag ggc gtg acc tcc ggc ggt tcg ggc gac    1153
Leu Ser Gly Asp Gln Ala Gln Gly Val Thr Ser Gly Gly Ser Gly Asp
        145                 150                 155 tgc acc tcc ggc ggc acg acc tac ttc cag ccg gtc aac gag atc ctg    1201
Cys Thr Ser Gly Gly Thr Thr Tyr Phe Gln Pro Val Asn Glu Ile Leu
            160                 165                 170 cag gcc tac ggt ctg acg ctg ctc acc cag tgaaccccga gtgaccggtt      1251
Gln Ala Tyr Gly Leu Thr Leu Leu Thr Gln
        175                 180
```

```
gaccgaccgc gtgggcgccg gcggcacgtc cgccggggcc cacgcacgtc ctagcccagc    1311
ttggtccgca cgccgcggc ggc                                              1334
```

<210> SEQ ID NO 2
<211> LENGTH: 377
<212> TYPE: PRT
<213> ORGANISM: Saccharopolyspora erythraea

<400> SEQUENCE: 2

```
Met Lys Arg Arg Leu Ala Ala Arg Val Thr Gly Ser Val Ile Phe
            -190                -185                -180

Ala Ala Gly Thr Ile Ala Ala Leu Thr Val Pro Ala Thr Ala Asn
            -175                -170                -165

Pro Thr Ala Pro Ala Pro Val Ala Ala Glu Ala Ala Thr Leu Met
            -160                -155                -150

Glu Ala Met Gln Arg Asp Leu Gly Leu Thr Ala Glu Gln Ala Ala
            -145                -140                -135

Glu Arg Leu Ala Asp Glu Ala Ala Thr Arg Ala Asp Gln Ser
            -130                -125                -120

Leu Arg Gly Thr Leu Gly Ser Ala Phe Gly Gly Ser His Tyr Asp
            -115                -110                -105

Ala Ala Leu Gly Lys Leu Val Val Gly Val Thr Asp Ala Gly Leu Leu
            -100                -95                 -90

Asp Glu Val Arg Ala Ala Gly Ala Asp Gly Leu Val Gln His Asn
            -85                 -80                 -75

Val Gln Gln Leu Asp Gly Val Ala Asp Gly Leu Asp Ala Gln Ser Ala
        -70                 -65                 -60

Arg Ala Pro Gln Ser Val Thr Gly Trp Tyr Val Asp Ser Ser Ser Asn
    -55                 -50                 -45

Ser Val Val Leu Thr Thr Ala Pro Gly Thr Ala Gly Gln Ala Thr Asp
-40                 -35                 -30                 -25

Phe Val Arg Ala Ser Gly Val Asp Ala Gly Ala Val Arg Val Glu
            -20                 -15                 -10

Ser Ala Glu Gln Pro Arg Thr Tyr Ala Asp Val Ile Gly Gly Asp Ala
        -5                  -1  1                   5

Tyr Tyr Ile Gly Ser Gly Ser Arg Cys Ser Val Gly Phe Ser Val Gln
        10                  15                  20

Gly Gly Phe Val Thr Ala Gly His Cys Gly Asn Gln Gly Asp Ser Thr
25                  30                  35                  40

Ser Gln Pro Ser Gly Thr Phe Glu Gly Ser Ser Phe Pro Gly Asn Asp
                45                  50                  55

Tyr Gly Trp Val Arg Thr Ala Ser Gly Glu Asn Pro Val Pro Leu Val
        60                  65                  70

Asn Asp Tyr Gln Gly Gly Thr Val Gly Val Ala Gly Ser Ser Glu Ala
    75                  80                  85

Ala Glu Gly Ala Ser Ile Cys Arg Ser Gly Ser Thr Thr Gly Trp His
90                  95                  100

Cys Gly Thr Val Glu Ala Lys Asn Gln Thr Val Arg Tyr Pro Gln Gly
105                 110                 115                 120

Thr Val Glu Gly Leu Thr Arg Thr Asn Val Cys Ala Glu Pro Gly Asp
                125                 130                 135

Ser Gly Gly Ser Trp Leu Ser Gly Asp Gln Ala Gln Gly Val Thr Ser
            140                 145                 150

Gly Gly Ser Gly Asp Cys Thr Ser Gly Gly Thr Thr Tyr Phe Gln Pro
```

<210> SEQ ID NO 3
<211> LENGTH: 1092
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(1089)
<220> FEATURE:
<221> NAME/KEY: sig_peptide
<222> LOCATION: (1)..(81)
<220> FEATURE:
<221> NAME/KEY: mat_peptide
<222> LOCATION: (541)..(1089)

<400> SEQUENCE: 3

```
                                                                      155                 160                 165
                                                                      Val Asn Glu Ile Leu Gln Ala Tyr Gly Leu Thr Leu Leu Thr Gln
                                                                              170                 175                 180 atg aag aaa ccg ttg ggg aaa att gtc gca agc acc gca cta ctc         45
Met Lys Lys Pro Leu Gly Lys Ile Val Ala Ser Thr Ala Leu Leu
-180                -175                -170 att tct gtt gct ttt agt tca tcg atc gca tcg gct gca aca ttg         90
Ile Ser Val Ala Phe Ser Ser Ser Ile Ala Ser Ala Ala Thr Leu
-165                -160                -155 atg gaa gcg atg caa cgt gat tta ggc ctt aca gct gaa caa gca        135
Met Glu Ala Met Gln Arg Asp Leu Gly Leu Thr Ala Glu Gln Ala
-150                -145                -140 gct gaa cgt ctt gct gac gaa gct gcg gca aca cgc gct gac caa        180
Ala Glu Arg Leu Ala Asp Glu Ala Ala Ala Thr Arg Ala Asp Gln
-135                -130                -125 tct ctt cgt ggc act ctt gga tct gcc ttc gga ggt agc cac tat        225
Ser Leu Arg Gly Thr Leu Gly Ser Ala Phe Gly Gly Ser His Tyr
-120                -115                -110 gat gcg gct ttg ggt aaa ctt gtt gtt ggc gtt act gac gct gga ctt    273
Asp Ala Ala Leu Gly Lys Leu Val Val Gly Val Thr Asp Ala Gly Leu
-105                -100                -95                 -90 tta gat gaa gtt cgt gct gct ggt gct gat ggt gaa ctt gta caa cat    321
Leu Asp Glu Val Arg Ala Ala Gly Ala Asp Gly Glu Leu Val Gln His
                -85                 -80                 -75 aac gtt caa cag tta gac ggt gtt gct gac gga ctt gat gca caa tca    369
Asn Val Gln Gln Leu Asp Gly Val Ala Asp Gly Leu Asp Ala Gln Ser
        -70                 -65                 -60 gca cgt gcg cct caa tct gta aca gga tgg tac gtt gat tct tca tct    417
Ala Arg Ala Pro Gln Ser Val Thr Gly Trp Tyr Val Asp Ser Ser Ser
        -55                 -50                 -45 aac tca gta gta ctt act aca gcg cct ggt act gct ggc caa gct act    465
Asn Ser Val Val Leu Thr Thr Ala Pro Gly Thr Ala Gly Gln Ala Thr
        -40                 -35                 -30 gac ttc gtt cgt gct tct gga gtt gat gcg ggt gct gtt cgt gta gtt    513
Asp Phe Val Arg Ala Ser Gly Val Asp Ala Gly Ala Val Arg Val Val
-25                 -20                 -15                 -10 gaa tca gct gaa caa ccg cgt act tat gcg gat gtt atc gga ggt gac    561
Glu Ser Ala Glu Gln Pro Arg Thr Tyr Ala Asp Val Ile Gly Gly Asp
                -5                  -1  1                   5 gct tac tat atc ggc tct gga tct cgc tgc tca gtt ggc ttc tct gtt    609
Ala Tyr Tyr Ile Gly Ser Gly Ser Arg Cys Ser Val Gly Phe Ser Val
                10                  15                  20 caa ggc gga ttc gta aca gct gga cat tgt ggt aac caa ggt gac tct    657
Gln Gly Gly Phe Val Thr Ala Gly His Cys Gly Asn Gln Gly Asp Ser
        25                  30                  35
```

```
act tct cag cca tct ggc act ttt gag ggt tct agc ttc cct ggt aat      705
Thr Ser Gln Pro Ser Gly Thr Phe Glu Gly Ser Ser Phe Pro Gly Asn
 40              45                  50                  55 gat tac ggt tgg gtt cgt act gct tct gga gag aac cct gtt cct ctt      753
Asp Tyr Gly Trp Val Arg Thr Ala Ser Gly Glu Asn Pro Val Pro Leu
                 60                  65                  70 gtt aac gat tac caa ggt ggt act gtt ggc gta gcg gga agc tct gaa      801
Val Asn Asp Tyr Gln Gly Gly Thr Val Gly Val Ala Gly Ser Ser Glu
             75                  80                  85 gca gct gaa gga gct tct atc tgc cgc tct ggt tct acg act ggt tgg      849
Ala Ala Glu Gly Ala Ser Ile Cys Arg Ser Gly Ser Thr Thr Gly Trp
         90                  95                 100 cat tgc ggt act gtt gaa gcg aaa aac cag act gta cgc tat cca caa      897
His Cys Gly Thr Val Glu Ala Lys Asn Gln Thr Val Arg Tyr Pro Gln
    105                 110                 115 gga acg gtt gaa ggc ttg act cgc act aac gta tgc gca gaa cct ggc      945
Gly Thr Val Glu Gly Leu Thr Arg Thr Asn Val Cys Ala Glu Pro Gly
120                 125                 130                 135 gac tct gga gga agc tgg ttg tct ggc gac caa gct caa gga gta aca      993
Asp Ser Gly Gly Ser Trp Leu Ser Gly Asp Gln Ala Gln Gly Val Thr
                140                 145                 150 tct gga ggc tct ggc gac tgt act tct gga gga act acg tat ttc caa     1041
Ser Gly Gly Ser Gly Asp Cys Thr Ser Gly Gly Thr Thr Tyr Phe Gln
            155                 160                 165 cca gta aac gaa atc ttg cag gct tac gga ctt aca ctt ctt aca caa     1089
Pro Val Asn Glu Ile Leu Gln Ala Tyr Gly Leu Thr Leu Leu Thr Gln
        170                 175                 180 taa                                                                 1092

<210> SEQ ID NO 4
<211> LENGTH: 363
<212> TYPE: PRT
<213> ORGANISM: Artificial Sequence
<220> FEATURE:
<223> OTHER INFORMATION: Synthetic Construct

<400> SEQUENCE: 4

Met  Lys Lys Pro Leu Gly  Lys Ile Val Ala Ser  Thr Ala Leu Leu
-180              -175                -170

Ile  Ser Val Ala Phe Ser  Ser Ser Ile Ala Ser  Ala Ala Thr Leu
-165              -160                -155

Met  Glu Ala Met Gln Arg  Asp Leu Gly Leu Thr  Ala Glu Gln Ala
-150              -145                -140

Ala  Glu Arg Leu Ala Asp  Glu Ala Ala Ala Thr  Arg Ala Asp Gln
-135              -130                -125

Ser  Leu Arg Gly Thr Leu  Gly Ser Ala Phe Gly  Gly Ser His Tyr
-120              -115                -110

Asp  Ala Ala Leu Gly Lys  Leu Val Val Gly Val  Thr Asp Ala Gly Leu
-105              -100                 -95                 -90

Leu Asp Glu Val Arg Ala Ala Gly Ala Asp Gly Glu Leu Val Gln His
                 -85                 -80                 -75

Asn Val Gln Gln Leu Asp Gly Val Ala Asp Gly Leu Asp Ala Gln Ser
            -70                 -65                 -60

Ala Arg Ala Pro Gln Ser Val Thr Gly Trp Tyr Val Asp Ser Ser Ser
        -55                 -50                 -45

Asn Ser Val Val Leu Thr Thr Ala Pro Gly Thr Ala Gly Gln Ala Thr
    -40                 -35                 -30
```

```
Asp Phe Val Arg Ala Ser Gly Val Asp Ala Gly Ala Val Arg Val Val
-25                 -20                 -15                 -10

Glu Ser Ala Glu Gln Pro Arg Thr Tyr Ala Asp Val Ile Gly Gly Asp
            -5              -1  1                   5

Ala Tyr Tyr Ile Gly Ser Gly Ser Arg Cys Ser Val Gly Phe Ser Val
            10              15                  20

Gln Gly Gly Phe Val Thr Ala Gly His Cys Gly Asn Gln Gly Asp Ser
    25              30                  35

Thr Ser Gln Pro Ser Gly Thr Phe Glu Gly Ser Ser Phe Pro Gly Asn
40              45                  50                  55

Asp Tyr Gly Trp Val Arg Thr Ala Ser Gly Glu Asn Pro Val Pro Leu
            60                  65                  70

Val Asn Asp Tyr Gln Gly Gly Thr Val Gly Val Ala Gly Ser Ser Glu
        75                  80                  85

Ala Ala Glu Gly Ala Ser Ile Cys Arg Ser Gly Ser Thr Thr Gly Trp
        90                  95                  100

His Cys Gly Thr Val Glu Ala Lys Asn Gln Thr Val Arg Tyr Pro Gln
    105                 110                 115

Gly Thr Val Glu Gly Leu Thr Arg Thr Asn Val Cys Ala Glu Pro Gly
120             125                 130                 135

Asp Ser Gly Gly Ser Trp Leu Ser Gly Asp Gln Ala Gln Gly Val Thr
                140                 145                 150

Ser Gly Gly Ser Gly Asp Cys Thr Ser Gly Gly Thr Thr Tyr Phe Gln
                155                 160                 165

Pro Val Asn Glu Ile Leu Gln Ala Tyr Gly Leu Thr Leu Leu Thr Gln
        170                 175                 180

<210> SEQ ID NO 5
<211> LENGTH: 183
<212> TYPE: PRT
<213> ORGANISM: Saccharopolyspora erythraea
<220> FEATURE:
<221> NAME/KEY: mat_peptide
<222> LOCATION: (1)..(183)

<400> SEQUENCE: 5

Ala Asp Val Ile Gly Gly Asp Ala Tyr Tyr Ile Gly Ser Gly Ser Arg
1               5                   10                  15

Cys Ser Val Gly Phe Ser Val Gln Gly Gly Phe Val Thr Ala Gly His
            20                  25                  30

Cys Gly Asn Gln Gly Asp Ser Thr Ser Gln Pro Ser Gly Thr Phe Glu
        35                  40                  45

Gly Ser Ser Phe Pro Gly Asn Asp Tyr Gly Trp Val Arg Thr Ala Ser
    50                  55                  60

Gly Glu Asn Pro Val Pro Leu Val Asn Asp Tyr Gln Gly Gly Thr Val
65                  70                  75                  80

Gly Val Ala Gly Ser Ser Glu Ala Ala Glu Gly Ala Ser Ile Cys Arg
            85                  90                  95

Ser Gly Ser Thr Thr Gly Trp His Cys Gly Thr Val Glu Ala Lys Asn
        100                 105                 110

Gln Thr Val Arg Tyr Pro Gln Gly Thr Val Glu Gly Leu Thr Arg Thr
    115                 120                 125

Asn Val Cys Ala Glu Pro Gly Asp Ser Gly Gly Ser Trp Leu Ser Gly
130                 135                 140

Asp Gln Ala Gln Gly Val Thr Ser Gly Gly Ser Gly Asp Cys Thr Ser
145                 150                 155                 160
```

```
Gly Gly Thr Thr Tyr Phe Gln Pro Val Asn Glu Ile Leu Gln Ala Tyr
            165                 170                 175

Gly Leu Thr Leu Thr Gln
        180

<210> SEQ ID NO 6
<211> LENGTH: 1596
<212> TYPE: DNA
<213> ORGANISM: Nocardiopsis sp.
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 6
acgtttggta cgggtaccgg tgtccgcatg tggccagaat gccccttgc gacagggaac      60 ggattcggtc ggtagcgcat cgactccgac aaccgcgagg tggccgttcg cgtcgccacg    120
ttctgcgacc gtcatgcgac ccatcatcgg gtgaccccac cgagctctga atggtccacc    180
gttctgacgg tctttccctc accaaaacgt gcacctatgg ttaggacgtt gtttaccgaa    240
tgtctcggtg aacgacaggg gccggacggt attcggcccc gatcccccgt tgatccccc     300
```

```
aggagagtag ggacccc atg cga ccc tcc ccc  gtt gtc tcc gcc atc  ggt     350
                   Met Arg Pro Ser Pro  Val Val Ser Ala Ile  Gly
                       -190                 -185
```

```
acg gga gcg ctg gcc ttc ggt ctg gcg  ctg tcc ggt acc ccg  ggt        395
Thr Gly Ala Leu Ala Phe Gly Leu Ala  Leu Ser Gly Thr Pro  Gly
            -180                 -175                 -170
```

```
gcc ctc gcg gcc acc gga gcg ctc ccc  cag tca ccc acc ccg  gag        440
Ala Leu Ala Ala Thr Gly Ala Leu Pro  Gln Ser Pro Thr Pro  Glu
            -165                 -160                 -155
```

```
gcc gac gcg gtc tcc atg cag gag gcg  ctc cag cgc gac ctc  gac        485
Ala Asp Ala Val Ser Met Gln Glu Ala  Leu Gln Arg Asp Leu  Asp
            -150                 -145                 -140
```

```
ctg acc tcc gcc gag gcc gag gag ctg  ctg gcc gcc cag gac  acc        530
Leu Thr Ser Ala Glu Ala Glu Glu Leu  Leu Ala Ala Gln Asp  Thr
            -135                 -130                 -125
```

```
gcc ttc gag gtc gac gag gcc gcg gcc  gag gcc gcc ggg gac  gcc        575
Ala Phe Glu Val Asp Glu Ala Ala Ala  Glu Ala Ala Gly Asp  Ala
            -120                 -115                 -110
```

```
tac ggc ggc tcc gtc ttc gac acc gag  agc ctg gaa ctg acc gtc ctg    623
Tyr Gly Gly Ser Val Phe Asp Thr Glu  Ser Leu Glu Leu Thr Val Leu
            -105                 -100                  -95
```

```
gtc acc gat gcc gcc gcg gtc gag gcc  gtg gag gcc acc ggc gcc ggg    671
Val Thr Asp Ala Ala Ala Val Glu Ala  Val Glu Ala Thr Gly Ala Gly
             -90                  -85                  -80
```

```
acc gag ctg gtc tcc tac ggc atc gac  ggt ctc gac gag atc gtc cag    719
Thr Glu Leu Val Ser Tyr Gly Ile Asp  Gly Leu Asp Glu Ile Val Gln
             -75                  -70                  -65
```

```
gag ctc aac gcc gcc gac gcc gtt ccc  ggt gtg gtc ggc tgg tac ccg    767
Glu Leu Asn Ala Ala Asp Ala Val Pro  Gly Val Val Gly Trp Tyr Pro
-60                   -55                  -50                  -45
```

```
gac gtg gcg ggt gac acc gtc gtc ctg  gag gtc ctg gag ggt tcc gga    815
Asp Val Ala Gly Asp Thr Val Val Leu  Glu Val Leu Glu Gly Ser Gly
                 -40                  -35                  -30
```

```
gcc gac gtc agc ggc ctg ctc gcg gac  gcc ggc gtg gac gcc tcg gcc    863
```

```
gtc gag gtg acc acg agc gac cag ccc gag ctc tac gcc gac atc atc      911
Val Glu Val Thr Thr Ser Asp Gln Pro Glu Leu Tyr Ala Asp Ile Ile
        -10                 -5                  -1   1 ggt ggt ctg gcc tac acc atg ggc ggc cgc tgt tcg gtc ggc ttc gcg      959
Gly Gly Leu Ala Tyr Thr Met Gly Gly Arg Cys Ser Val Gly Phe Ala
 5                  10                  15                  20 gcc acc aac gcc gcc ggt cag ccc ggg ttc gtc acc gcc ggt cac tgc     1007
Ala Thr Asn Ala Ala Gly Gln Pro Gly Phe Val Thr Ala Gly His Cys
                25                  30                  35 ggc cgc gtg ggc acc cag gtg acc atc ggc aac ggc agg ggc gtc ttc     1055
Gly Arg Val Gly Thr Gln Val Thr Ile Gly Asn Gly Arg Gly Val Phe
         40                  45                  50 gag cag tcc gtc ttc ccc ggc aac gac gcg gcc ttc gtc cgc ggt acg     1103
Glu Gln Ser Val Phe Pro Gly Asn Asp Ala Ala Phe Val Arg Gly Thr
             55                  60                  65 tcc aac ttc acg ctg acc aac ctg gtc agc cgc tac aac acc ggc ggg     1151
Ser Asn Phe Thr Leu Thr Asn Leu Val Ser Arg Tyr Asn Thr Gly Gly
 70                  75                  80 tac gcc acg gtc gcc ggt cac aac cag gcc ccc atc ggc tcc tcc gtc     1199
Tyr Ala Thr Val Ala Gly His Asn Gln Ala Pro Ile Gly Ser Ser Val
 85                  90                  95                 100 tgc cgc tcc ggc tcc acc acc ggt tgg cac tgc ggc acc atc cag gcc     1247
Cys Arg Ser Gly Ser Thr Thr Gly Trp His Cys Gly Thr Ile Gln Ala
                105                 110                 115 cgc ggc cag tcg gtg agc tac ccc gag ggc acc gtc acc aac atg acc     1295
Arg Gly Gln Ser Val Ser Tyr Pro Glu Gly Thr Val Thr Asn Met Thr
         120                 125                 130 cgg acc acc gtg tgc gcc gag ccc ggc gac tcc ggc ggc tcc tac atc     1343
Arg Thr Thr Val Cys Ala Glu Pro Gly Asp Ser Gly Gly Ser Tyr Ile
             135                 140                 145 tcc ggc acc cag gcc cag ggc gtg acc tcc ggc ggc tcc ggc aac tgc     1391
Ser Gly Thr Gln Ala Gln Gly Val Thr Ser Gly Gly Ser Gly Asn Cys
 150                 155                 160 cgc acc ggc ggg acc acc ttc tac cag gag gtc acc ccc atg gtg aac     1439
Arg Thr Gly Gly Thr Thr Phe Tyr Gln Glu Val Thr Pro Met Val Asn
165                  170                 175                 180 tcc tgg ggc gtc cgt ctc cgg acc tgatccccgc ggttccaggc ggaccgacgg   1493
Ser Trp Gly Val Arg Leu Arg Thr
                185 tcgtgacctg agtaccaggc gtccccgccg cttccagcgg cgtccgcacc ggggtgggac   1553 cgggcgtggc cacggcccca cccgtgaccg gaccgcccgg cta                    1596

<210> SEQ ID NO 7
<211> LENGTH: 382
<212> TYPE: PRT
<213> ORGANISM: Nocardiopsis sp.

<400> SEQUENCE: 7

Met Arg Pro Ser Pro  Val Val Ser Ala Ile  Gly Thr Gly Ala Leu
              -190                 -185                 -180

Ala Phe Gly Leu Ala  Leu Ser Gly Thr Pro  Gly Ala Leu Ala Ala
              -175                 -170                 -165

Thr Gly Ala Leu Pro  Gln Ser Pro Thr Pro  Glu Ala Asp Ala Val
              -160                 -155                 -150

Ser Met Gln Glu Ala  Leu Gln Arg Asp Leu  Asp Leu Thr Ser Ala
              -145                 -140                 -135
```

```
Glu Ala Glu Glu Leu Leu Ala Ala Gln Asp Thr Ala Phe Glu Val
            -130               -125              -120

Asp Glu Ala Ala Ala Glu Ala Ala Gly Asp Ala Tyr Gly Gly Ser
            -115              -110              -105

Val Phe Asp Thr Glu Ser Leu Glu Leu Thr Val Leu Val Thr Asp Ala
            -100               -95               -90

Ala Ala Val Glu Ala Val Glu Ala Thr Gly Ala Gly Thr Glu Leu Val
             -85                -80               -75

Ser Tyr Gly Ile Asp Gly Leu Asp Glu Ile Val Gln Glu Leu Asn Ala
         -70                -65               -60

Ala Asp Ala Val Pro Gly Val Gly Trp Tyr Pro Asp Val Ala Gly
         -55              -50               -45

Asp Thr Val Val Leu Glu Val Leu Glu Gly Ser Gly Ala Asp Val Ser
-40              -35               -30                 -25

Gly Leu Leu Ala Asp Ala Gly Val Asp Ala Ser Ala Val Glu Val Thr
             -20               -15                -10

Thr Ser Asp Gln Pro Glu Leu Tyr Ala Asp Ile Ile Gly Gly Leu Ala
         -5              -1  1               5

Tyr Thr Met Gly Gly Arg Cys Ser Val Gly Phe Ala Ala Thr Asn Ala
         10              15              20

Ala Gly Gln Pro Gly Phe Val Thr Ala Gly His Cys Gly Arg Val Gly
25           30              35                  40

Thr Gln Val Thr Ile Gly Asn Gly Arg Gly Val Phe Glu Gln Ser Val
                 45              50              55

Phe Pro Gly Asn Asp Ala Ala Phe Val Arg Gly Thr Ser Asn Phe Thr
             60              65              70

Leu Thr Asn Leu Val Ser Arg Tyr Asn Thr Gly Gly Tyr Ala Thr Val
         75              80              85

Ala Gly His Asn Gln Ala Pro Ile Gly Ser Ser Val Cys Arg Ser Gly
         90              95              100

Ser Thr Thr Gly Trp His Cys Gly Thr Ile Gln Ala Arg Gly Gln Ser
105              110             115                 120

Val Ser Tyr Pro Glu Gly Thr Val Thr Asn Met Thr Arg Thr Thr Val
             125             130             135

Cys Ala Glu Pro Gly Asp Ser Gly Ser Tyr Ile Ser Gly Thr Gln
             140             145             150

Ala Gln Gly Val Thr Ser Gly Gly Ser Gly Asn Cys Arg Thr Gly Gly
         155             160             165

Thr Thr Phe Tyr Gln Glu Val Thr Pro Met Val Asn Ser Trp Gly Val
         170             175             180

Arg Leu Arg Thr
185

<210> SEQ ID NO 8
<211> LENGTH: 378
<212> TYPE: PRT
<213> ORGANISM: Saccharomonospora xinjiangensis XJ-54

<400> SEQUENCE: 8

Met Asn Arg Lys Asn Ala Ala Arg Leu Ile Ala Ser Val Thr Leu Ala
1               5                   10                  15

Ala Gly Thr Ala Val Ala Phe Thr Leu Pro Ala Thr Ala Ala Pro Ala
            20                  25                  30

Ala Asp Ala Val Val Pro Ala Thr Ala Ala Asp Pro Val Val Gln Ala
        35                  40                  45
```

Met Gln Arg Asp Leu Gly Leu Thr Lys Gln Glu Ala Glu Gln Arg Leu
    50                  55                  60

Arg Ser Glu Ala Glu Ala Arg Glu Val His Glu Thr Val Ser Glu Arg
65                  70                  75                  80

Leu Gly Ser Asp Phe Ala Gly Ala His Tyr Asp Ala Gly Arg Gly Thr
                85                  90                  95

Leu Val Val Gly Val Thr Asp Ala Ala Glu Phe Ser Glu Val Arg Glu
            100                 105                 110

Ala Gly Ala Thr Pro Arg Leu Val Glu His Thr Val Ala Asp Leu Glu
        115                 120                 125

Ser Ala Ala Glu Lys Leu Asp Ala Lys Glu Ser Arg Ala Pro Glu Ser
    130                 135                 140

Val Thr Gly Trp Tyr Val Asp Ile Glu Ala Asn Ser Val Val Val Thr
145                 150                 155                 160

Thr Lys Pro Gly Thr Ala Gly Gln Ala Glu Arg Phe Val Ser Arg Ala
                165                 170                 175

Gly Val Asp Ala Asp Ala Val Asp Val Glu Ser Lys Glu Ser Pro
            180                 185                 190

Arg Ala Leu Met Asp Ile Ile Gly Gly Asn Ala Tyr Tyr Met Gly Ser
        195                 200                 205

Gly Gly Arg Cys Ser Val Gly Phe Ser Val Gln Gly Gly Phe Val Thr
    210                 215                 220

Ala Gly His Cys Gly Thr Thr Gly Thr Thr Thr Ser Ser Pro Thr Gly
225                 230                 235                 240

Arg Phe Ala Gly Ser Ser Phe Pro Gly Asn Asp Tyr Ala Phe Val Arg
                245                 250                 255

Thr Gly Ser Gly Asp Thr Leu Arg Pro Trp Val Asn Met Tyr Asn Gly
            260                 265                 270

Ser Ala Arg Val Val Ser Gly Ser Glu Ala Pro Val Gly Ser Ser
        275                 280                 285

Ile Cys Arg Ser Gly Ser Thr Thr Gly Trp His Cys Gly Thr Val Glu
    290                 295                 300

Ala Lys Asn Gln Thr Val Arg Tyr Pro Gln Gly Thr Val Tyr Gly Leu
305                 310                 315                 320

Thr Arg Thr Asn Val Cys Ala Glu Pro Gly Asp Ser Gly Gly Ser Phe
                325                 330                 335

Ile Ser Gly Asn Gln Ala Gln Gly Met Thr Ser Gly Ser Gly Asn
            340                 345                 350

Cys Thr Trp Gly Gly Thr Thr Tyr Phe Gln Pro Val Asn Glu Val Leu
        355                 360                 365

Asn Ala Tyr Gly Leu Arg Leu Ile Thr Gly
    370                 375

<210> SEQ ID NO 9
<211> LENGTH: 375
<212> TYPE: PRT
<213> ORGANISM: Saccharomonospora paurometabolica YIM 90007

<400> SEQUENCE: 9

Met Lys Arg Thr Arg Asn Gly Phe Ala Ala Arg Ala Gly Ala Ala Ala
1               5                   10                  15

Val Leu Ala Ala Gly Thr Ala Ala Ala Phe Ala Leu Pro Ala Ser Ala
            20                  25                  30

Gln Pro Ala Pro Met Asp Val Asp Pro Gly Met Val Gln Ala Met Glu

```
                35                  40                  45
Arg Asp Leu Gly Leu Ser Gly Thr Gln Ala Glu Gln Arg Leu Arg Ser
 50                  55                  60

Glu Ala Thr Ala Arg Ala Val Asp Glu Thr Val Arg Ala Glu Leu Gly
 65                  70                  75                  80

Asp Ser Phe Gly Gly Ser Phe Tyr Asp Ala Asp Lys Gly Gly Leu Val
                 85                  90                  95

Val Ser Val Thr Asp Pro Ala Gln Leu Arg Glu Ala Arg Ala Ala Gly
            100                 105                 110

Ala Glu Ala Arg Met Val Asp Asp Ser Ala Ala Glu Leu Glu Ala Ala
        115                 120                 125

Ala Asn Arg Leu Asn Arg Ala Glu Ser Arg Ala Pro Gly Ser Val Thr
    130                 135                 140

Gly Trp Tyr Val Asp Val Glu Arg Asn Ser Val Val Thr Thr Thr
145                 150                 155                 160

Pro Gly Thr Ala Ala Gly Ala Glu Glu Phe Val Ala Ser Ala Gly Val
                165                 170                 175

Asp Ala Asp Thr Ala Glu Val Val Glu Ser Ala Glu Arg Pro Arg Ala
            180                 185                 190

Leu Met Asp Val Val Gly Gly Asn Ala Tyr Tyr Met Gly Ser Gly Gly
        195                 200                 205

Arg Cys Ser Val Gly Phe Ala Val Asn Gly Gly Phe Val Thr Ala Gly
    210                 215                 220

His Cys Gly Ser Thr Gly Glu Ser Thr Ser Gln Pro Ser Gly Thr Phe
225                 230                 235                 240

Ala Gly Ser Ser Phe Pro Tyr Asn Asp Tyr Ala Tyr Val Glu Thr Gly
                245                 250                 255

Ser Asp Asp Thr Pro Arg Pro Tyr Val Asn Thr Tyr Ser Gly Thr Arg
            260                 265                 270

Thr Val Ser Gly Ser Asn Glu Ala Pro Val Gly Ser Ser Ile Cys Arg
        275                 280                 285

Ser Gly Ser Thr Thr Gly Trp His Cys Gly Thr Val Glu Ala Lys Asn
    290                 295                 300

Gln Thr Val Arg Tyr Ser Gln Gly Ala Val Tyr Gly Met Thr Arg Thr
305                 310                 315                 320

Asp Val Cys Ala Glu Pro Gly Asp Ser Gly Ser Phe Ile Ser Gly
                325                 330                 335

Asn Gln Ala Gln Gly Met Thr Ser Gly Gly Ser Gly Asn Cys Thr Trp
            340                 345                 350

Gly Gly Thr Thr Tyr Phe Gln Pro Val Asn Glu Ala Leu Asn Ala Tyr
        355                 360                 365

Gly Leu Ser Leu Val Thr Gly
    370                 375

<210> SEQ ID NO 10
<211> LENGTH: 432
<212> TYPE: PRT
<213> ORGANISM: Kribbella flavida

<400> SEQUENCE: 10

Met Ser Ala Ala Gly Leu Ala Ala Val Thr Phe Thr Pro Val Ala
 1               5                  10                  15

Thr Ala Leu Arg Pro Ala Pro Pro Pro Ala Ala Ser Ala Asp
            20                  25                  30
```

```
Ala Gln Asp Ser Ala Pro Met Leu Ala Ala Leu Ala Arg Asp Leu Lys
         35                  40                  45

Ile Thr Pro Asp Glu Ala Arg Ala Arg Leu Ala Arg Glu Thr Thr Ala
 50                  55                  60

Ala Glu Ala Glu Arg Phe Leu Arg Thr Thr Leu Gly Thr Ala Phe Ala
 65                  70                  75                  80

Gly Ala Trp Leu Asp Arg Asp Ala Ser Thr Leu Thr Val Gly Ile Thr
                 85                  90                  95

Asp Pro Ala Arg Ala Gly Leu Val Arg Ala Val Gly Ala Val Pro Lys
                100                 105                 110

Pro Val Pro Arg Gly Leu Asp Gln Leu Asp Ala Leu Lys Asn Arg Leu
            115                 120                 125

Asp Ser Asn Ala Ala Arg Ala Pro Arg Thr Val Pro Gly Trp Tyr Val
130                 135                 140

Asp Val Thr Thr Asn Gln Leu Val Ile Leu Ser Arg Arg Gly Ala Thr
145                 150                 155                 160

Ala Gln Ala Lys Ala Phe Ala Lys Val Ser Gly Ile Glu Gly Ser Thr
                165                 170                 175

Val Arg Phe Gln Asp Ser Ala Glu Thr Pro Arg Pro Leu Ile Asp Ile
            180                 185                 190

Ile Gly Gly Asn Ala Tyr Tyr Ile Gly Ser Gly Ser Arg Cys Ser Val
        195                 200                 205

Gly Phe Ala Val Thr Gly Gly Phe Val Thr Ala Gly His Cys Gly Arg
    210                 215                 220

Leu Gly Ala Thr Thr Gln Pro Ser Gly Thr Phe Ala Gly Ser Ser
225                 230                 235                 240

Phe Pro Gly Asn Asp Tyr Ala Trp Val Arg Val Ala Ala Gly Asn Thr
                245                 250                 255

Pro Arg Ala Leu Val Asn Arg Tyr Pro Gly Thr Val Pro Val Ala Gly
            260                 265                 270

Ser Thr Glu Ala Ala Val Gly Ser Ser Val Cys Arg Ser Gly Ser Thr
        275                 280                 285

Thr Gly Trp Arg Cys Gly Ile Ile Gln Gln Lys Asn Ala Ser Val Thr
    290                 295                 300

Tyr Pro Glu Gly Thr Ile Thr Gly Leu Thr Arg Thr Asn Ala Cys Ala
305                 310                 315                 320

Glu Pro Gly Asp Ser Gly Gly Ser Trp Leu Thr Gly Asp Gln Ala Gln
                325                 330                 335

Gly Val Thr Ser Gly Gly Ser Gly Asn Cys Thr Ser Gly Gly Val Ile
            340                 345                 350

Tyr Phe Gln Pro Val Asn Glu Ile Leu Thr Ala Tyr Asn Leu Thr Leu
        355                 360                 365

Thr Val Ser Gly Ser Thr Pro Pro Thr Thr Pro Thr Thr Pro Thr Pro
    370                 375                 380

Gly Glu Thr Thr Trp Arg Ala Gly Thr Ala Tyr Pro Leu Gly Ala Val
385                 390                 395                 400

Val Thr Tyr Ser Gly Arg Arg Tyr Gln Cys Gln Gln Gly His Thr Ala
                405                 410                 415

Gln Pro Gly Trp Glu Pro Pro Asn Val Pro Ala Leu Trp Leu Gln Ile
            420                 425                 430

<210> SEQ ID NO 11
<211> LENGTH: 381
<212> TYPE: PRT
```

<213> ORGANISM: Saccharomonospora viridis

<400> SEQUENCE: 11

Met Leu Pro Lys Lys His Arg Leu Val Ala Arg Met Thr Ala Thr Ala
1               5                   10                  15

Met Leu Ala Ala Gly Thr Ala Ala Val Ala Leu Pro Ala Thr Ala
            20                  25                  30

Glu Thr Val Thr Pro Gln Thr Glu Val Thr Ala Glu Ala Asp Pro Met
            35                  40                  45

Leu Gln Ala Met Gln Arg Asp Leu Gly Leu Thr Ala Gln Glu Ala Gln
50                  55                  60

Gln Arg Leu Glu Gln Ser Val Ala Arg Thr Leu Asp Glu Thr Leu
65                  70                  75                  80

Arg Ala Lys Leu Gln Asp Asn Phe Gly Gly Ser Tyr Tyr Asp Ala Asp
                85                  90                  95

Thr Gly Thr Leu Val Val Gly Val Thr Glu Ala Ser Ala Leu Asp Asp
            100                 105                 110

Val Arg Ala Ala Gly Ala Lys Ala Lys Leu Val Asp Ala Ser Ile Asp
            115                 120                 125

Glu Leu Asn Thr Ala Val Asp Arg Leu Asp Arg Lys Glu Ser Ser Ala
130                 135                 140

Pro Glu Ser Val Thr Gly Trp Tyr Val Asp Val Lys Asn Asn Ser Val
145                 150                 155                 160

Val Val Thr Thr Ala Pro Gly Thr Ala Ala Gln Ala Glu Lys Phe Val
                165                 170                 175

Ala Ala Ser Gly Val Asp Gly Asp Asn Val Glu Ile Val Glu Ser Thr
            180                 185                 190

Glu Gln Pro Arg Thr Phe Met Asp Val Ile Gly Gly Asn Ala Tyr Tyr
            195                 200                 205

Met Gly Asn Gly Gly Arg Cys Ser Val Gly Phe Thr Val Gln Gly Gly
210                 215                 220

Phe Val Thr Ala Gly His Cys Gly Thr Thr Gly Thr Ser Thr Ser Ser
225                 230                 235                 240

Pro Ser Gly Thr Phe Ala Gly Ser Ser Phe Pro Gly Asn Asp Tyr Ala
                245                 250                 255

Phe Val Arg Thr Gly Ser Gly Asp Thr Leu Arg Pro Trp Val Asn Met
            260                 265                 270

Tyr Asn Gly Ser Ala Arg Val Val Ser Gly Ser Ser Val Ala Pro Val
            275                 280                 285

Gly Ser Ser Ile Cys Arg Ser Gly Ser Thr Thr Gly Trp His Cys Gly
290                 295                 300

Gln Val Gln Ala Phe Asn Gln Thr Val Arg Tyr Ala Glu Gly Thr Val
305                 310                 315                 320

Thr Gly Leu Thr Arg Thr Asn Val Cys Ala Glu Pro Gly Asp Ser Gly
                325                 330                 335

Gly Ser Phe Ile Ser Gly Asn Gln Ala Gln Gly Met Thr Ser Gly Gly
            340                 345                 350

Ser Gly Asn Cys Thr Phe Gly Gly Thr Thr Tyr Phe Gln Pro Val Asn
            355                 360                 365

Glu Val Leu Ser Ala Tyr Asn Leu Arg Leu Ile Thr Gly
370                 375                 380

<210> SEQ ID NO 12
<211> LENGTH: 477

<212> TYPE: PRT
<213> ORGANISM: Saccharothrix espanaensis

<400> SEQUENCE: 12

```
Met Ser Thr Leu Leu Arg Pro Leu Ala Leu Ala Ala Leu Val Ala
1               5                   10                  15

Ala Gly Ala Leu Ala Pro Thr Ala Gln Ala Ala Pro Ala Asp Gln Ser
            20                  25                  30

Thr Glu Ile Leu Ala Ala Ile Gln Arg Asp Leu Gly Leu Asn Ala Ala
        35                  40                  45

Gln Ala Glu Asp Arg Leu Ser Ala Asp Arg Thr Ser Ser Asp Thr Ala
50                  55                  60

Arg Asp Leu Arg Lys Arg Leu Asp Asp Arg Phe Gly Gly Ala Trp Ile
65                  70                  75                  80

Asp Ala Ser Gly Thr Leu Thr Val Gly Val Thr Thr Gln Ala Asp Leu
                85                  90                  95

Ala Gln Val Gly Arg Gly Arg Gly Arg Leu Val Gln Arg Ser Glu His
            100                 105                 110

Asp Leu Asp Ala Val Lys Ser Thr Leu Asp Arg Asn Val Ala Lys Ala
        115                 120                 125

Pro Lys Ser Val Pro Gly Trp Tyr Val Asp Leu Pro Thr Asn Thr Val
130                 135                 140

Val Val Lys Ser Gln Pro Glu Lys Leu Ser Ala Ala Arg Ala Phe Val
145                 150                 155                 160

Ala Ala Ser Gly Val Asp Ala Ala Val Arg Tyr Val Ala Thr Thr
                165                 170                 175

Glu Ala Pro Arg Pro Leu Ile Asp Val Val Gly Gly Asn Ala Tyr Asn
            180                 185                 190

Ile Gly Ser Gly Thr Arg Cys Ser Val Gly Phe Ser Val Asn Gly Gly
        195                 200                 205

Phe Ile Thr Ala Gly His Cys Gly Thr Thr Gly Ala Ser Thr Ser Asn
210                 215                 220

Pro Ser Gly Ser Phe Arg Gly Ser Ser Phe Pro Gly Asn Asp Tyr Ala
225                 230                 235                 240

Trp Val Gln Val Ala Ala Gly Asn Thr Pro Arg Gly Leu Val Asn Asn
                245                 250                 255

Tyr Ser Gly Gly Thr Val Ser Val Ala Gly Ser Gln Asp Ala Ala Val
            260                 265                 270

Gly Ala Thr Val Cys Arg Ser Gly Ser Thr Thr Gly Trp His Cys Gly
        275                 280                 285

Thr Ile Gln Ala Arg Asn Ser Ser Val Ser Tyr Pro Gln Gly Thr Val
290                 295                 300

Thr Gly Leu Ile Gln Thr Thr Val Cys Ala Glu Pro Gly Asp Ser Gly
305                 310                 315                 320

Gly Ser Leu Leu Ala Gly Thr Gln Ala Gln Gly Val Thr Ser Gly Gly
                325                 330                 335

Ser Gly Asn Cys Ser Ser Gly Gly Thr Thr Tyr Phe Gln Pro Val Asn
            340                 345                 350

Glu Ile Leu Gln Thr Tyr Gly Leu Thr Leu Val Thr Gly Gly Gly Gly
        355                 360                 365

Thr Pro Asn Pro Pro Thr Gly Cys Ala Thr Ala Glu Ala Arg Tyr Thr
370                 375                 380

Gly Ser Leu Ala Ala Gly Gly Gln Val Tyr Gln Pro Asn Asn Ser Tyr
385                 390                 395                 400
```

Tyr Gln Ser Thr Val Ser Gly Ala His Val Gly Cys Leu Val Gly Pro
            405                 410                 415

Thr Gly Ala Asp Phe Asp Leu Tyr Leu Gln Lys Trp Asn Gly Ser Ser
        420                 425                 430

Trp Ala Val Val Ala Lys Gly Asp Ser Pro Gly Ala Asn Glu Thr Val
            435                 440                 445

Thr Tyr Asn Gly Thr Ala Gly Tyr Tyr Arg Phe Gln Val His Ala Tyr
    450                 455                 460

Ser Gly Ser Gly Ser Tyr Thr Leu Gly Val Thr Asn Pro
465                 470                 475

<210> SEQ ID NO 13
<211> LENGTH: 435
<212> TYPE: PRT
<213> ORGANISM: Saccarothrix espanaensis

<400> SEQUENCE: 13

Met Thr Arg Arg Ile Ala Ala Val Ala Val Thr Val Leu Ser Ala
1               5                   10                  15

Ala Gly Val Ala Ala Ala Leu Thr Thr Ser Ala Thr Ala Gly Pro Pro
            20                  25                  30

Thr Ala Ala Gln Glu Asp Gly Val Ile Ala Ala Met Ala Arg Asp Phe
        35                  40                  45

Lys Ile Ser Pro Asp Gln Ala Arg Ala Arg Ile Gly Arg Glu Ala Lys
    50                  55                  60

Ala Ala Thr Thr Glu Gln Ser Leu Lys Thr Lys Leu Gly Ala Asp Tyr
65                  70                  75                  80

Ala Gly Ala Trp Leu Asn Gly Asp Ala Thr Glu Phe Thr Val Ala Val
                85                  90                  95

Thr Ser Gln Ala Gln Ile Gln Ala Val Lys Asp Ala Gly Ala Thr Pro
            100                 105                 110

Lys Val Val Lys Arg Ser Gln Ile Gln Leu Asp Thr Leu Lys Ser Lys
        115                 120                 125

Leu Asp Ala Asn Lys Asn Ala Pro Lys Asp Val Pro Ala Trp Tyr Val
    130                 135                 140

Asp Val Gln Ser Asn Ser Val Val Leu Ala Arg Asn Thr Asp Ser
145                 150                 155                 160

Ala Lys Ser Phe Ile Gln Ala Ser Gly Val Asp Ala Ala Asp Val Arg
                165                 170                 175

Ile Glu Gln Ser Thr Glu Asn Pro Arg Ala Leu Ile Asp Val Ile Gly
            180                 185                 190

Gly Asn Ala Tyr Tyr Met Gly Gly Gly Arg Cys Ser Val Gly Phe
        195                 200                 205

Ser Val Asn Gly Gly Phe Val Thr Ala Gly His Cys Gly Arg Thr Gly
    210                 215                 220

Ser Thr Thr Thr Gln Pro Ser Gly Thr Phe Ala Gly Ser Thr Phe Pro
225                 230                 235                 240

Gly Arg Asp Tyr Ala Trp Val Arg Val Ser Ala Gly Asn Thr Met Arg
                245                 250                 255

Gly Leu Val Asn Arg Tyr Pro Gly Thr Val Gly Val Lys Gly Ser Thr
            260                 265                 270

Glu Ala Ala Val Gly Ala Ser Val Cys Arg Ser Gly Ser Thr Thr Gly
        275                 280                 285

Trp His Cys Gly Thr Ile Gln Gln Lys Asn Thr Ser Val Thr Tyr Pro

```
                      290                 295                 300
Glu Gly Thr Ile Ser Gly Val Thr Arg Thr Asn Ala Cys Ala Glu Pro
305                 310                 315                 320

Gly Asp Ser Gly Gly Ser Trp Leu Ser Gly Asp Gln Ala Gln Gly Val
                325                 330                 335

Thr Ser Gly Gly Ser Gly Asn Cys Ser Ser Gly Gly Thr Thr Tyr Tyr
                340                 345                 350

Gln Pro Val Asn Pro Ile Leu Gln Ala Tyr Gly Leu Gln Leu Val Leu
                355                 360                 365

Asp Gly Gly Gly Thr Pro Thr Thr Gly Pro Thr Thr Thr Ser Asn
                370                 375                 380

Pro Gly Gly Gly Thr Ser Trp Gln Pro Gly Val Ala Tyr Ala Ala Gly
385                 390                 395                 400

Thr Asn Val Thr Tyr Ser Gly Val Gly Tyr Arg Cys Leu Gln Gly His
                405                 410                 415

Thr Ser Gln Thr Gly Trp Asp Pro Pro Ala Val Pro Ala Leu Trp Ala
                420                 425                 430

Arg Val Gly
        435

<210> SEQ ID NO 14
<211> LENGTH: 27
<212> TYPE: PRT
<213> ORGANISM: Artificial Sequence
<220> FEATURE:
<223> OTHER INFORMATION: Bacillus lentus signal peptide
<220> FEATURE:
<221> NAME/KEY: sig_peptide
<222> LOCATION: (1)..(27)

<400> SEQUENCE: 14

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```

POLYPEPTIDES HAVING PROTEASE ACTIVITY

CROSS-REFERENCE TO RELATED APPLICATIONS

This application is a 35 U.S.C. 371 national application of PCT/EP2014/052218 filed Feb. 5, 2014, which claims priority or the benefit under 35 U.S.C. 119 of European application no. 13154179.9 filed Feb. 6, 2013 and U.S. provisional application No. 61/763,518 filed Feb. 12, 2013. The content of each application is fully incorporated herein by reference.

REFERENCE TO A SEQUENCE LISTING

This application contains a Sequence Listing in computer readable form, which is incorporated hereiy reference.

BACKGROUND OF THE INVENTION

1. Field of the Invention

The present invention relates to isolated polypeptides having protease activity, and the use of isolated polypeptides having protease activity in animal feed. It also relates to the use of isolated nucleic acid sequences encoding the proteases in the recombinant production of isolated polypeptides having protease activity and isolated nucleic acid sequences encoding the proteases. The invention also relates to nucleic acid constructs, vectors, and host cells, including plant and animal cells, comprising the nucleic acid sequences, as well as methods for producing and using the proteases, particularly using the proteases in animal feed.

2. Background of the Invention

In the use of proteases in animal feed (in vivo), and/or the use of such proteases for treating vegetable proteins (in vitro) it is noted that proteins are essential nutritional factors for animals and humans. Humans and livestock usually get the necessary proteins from vegetable protein sources. Important vegetable protein sources are e.g. oilseed crops, legumes and cereals.

When e.g. soybean meal is included in the feed of mono-gastric animals such as pigs and poultry, a significant proportion of the soybean meal is not digested efficiently (the apparent ileal protein digestibility in piglets, growing pigs and poultry such as broilers, laying hens and roosters is only around 80%).

The gastrointestinal tract of animals consists of a series of segments each representing different pH environments. In mono-gastric animals such as pigs and poultry and many types of fish, the stomach is strongly acidic with a pH potentially as low as 1-2, while the intestine has a more neutral pH of around 6-7. Apart from the stomach and intestine, poultry also have a crop preceding the stomach. The pH in the crop is mostly determined by the feed ingested and hence typically lies in the range of pH 4-6. Protein digestion by a protease may occur along the entire digestive tract, provided that the protease is active and survives the conditions in the digestive tract. Hence, proteases which are highly acid stable and so can survive in the gastric environment and at the same time are efficiently active at the broad range of physiological pH of the digestive tract in the target animal are especially desirable.

Since animal feed is often formulated in pelleted form, in which steam is applied in the pelleting process, it is also desirable that proteases used in animal feed are capable of remaining active after exposure to said steam treatment.

In order to produce a protease for industrial use, it is important that the protease is produced in high yields making the product available in sufficient quantities in order to be able to provide the protease at a favourable price.

DESCRIPTION OF THE RELATED ART

Proteases of the S1 group isolated from *Saccharopolyspora* are known in the art. Oliynyk et al have reported a serine protease from *Saccharopolyspora erythraea* in 'Complete genome sequence of the erythromycin-producing bacterium *Saccharopolyspora erythraea* NRRL23338', 2007, *Nat. Biotechnol.* 25:447-453 which has been submitted to EMBL/GenBank (accession number EMBL: AM420293, SEQ ID NO: 1 herein). The amino acid sequence is registered with Uniprot number A4F726 (SEQ ID NO: 2 herein) and the mature amino acid sequence is disclosed in SEQ ID NO: 5.

Lucas et al have submitted a protease from *Saccharomonospora xinjiangensis* XJ-54 (Uniprot: I0V8H8, SEQ ID NO: 8) to EMBL/Genbank having 76.5% homology to sequence identity to SEQ ID NO: 5. Lucas et al have submitted an endopeptidase from *Saccharomonospora paurometabolica* YIM 90007 (Uniprot: G4J6Q2, SEQ ID NO: 9) having 74.7% sequence identity to SEQ ID NO: 5 to EMBL/Genbank.

Lucas et al have submitted the Chymotrypsin-like protease from *Kribbella flavida* (Uniprot: D2PRB9, SEQ ID NO: 10) having 74.7% homology to sequence identity to SEQ ID NO: 5 to EMBL/Genbank. Pati et al. have disclosed a serine protease from *Saccharomonospora viridis* in "Complete genome sequence of *Saccharomonospora viridis* type strain (P101)", 2009, *Stand. Genomic Sci.* 1:141-149 (Uniprot: C7MV18, SEQ ID NO: 11) with 73.8% sequence homology to SEQ ID NO: 5. Strobel et al have published 2 proteases from *Saccharothrix espanaensis* DSM 44229 having 74.3% and 73.6% sequence identity to to SEQ ID NO: 5 (Uniprot: K0JWC2, SEQ ID NO: 12 and K0JQQ4, SEQ ID NO: 13 respectively) in 'Complete genome sequence of *Saccharothrix espanaensis* DSM 44229T and comparison to the other completely sequenced Pseudonocardiaceae', 2012, *BMC Genomics,* 13:465-465.

The next closest *Saccharopolyspora* protease identified was submitted to EMBL/Genbank (Uniprot A4FNQ0) with 69.6% sequence identity to SEQ ID NO: 5. Other enzymes have less than 74% sequence identity to SEQ ID NO: 5.

WO 05/052146 and WO 05/052161 describe a number of serine proteases used for animal feed having an identity to the protease of SEQ ID NO: 5 of 67-73%.

WO 95/28850 discloses the combination of a phytase and one or more microbial proteolytic enzymes to improve the solubility of vegetable proteins. WO 01/58275 discloses the use of acid stable proteases of the subtilisin family in animal feed. WO 01/58276 discloses the use of acid-stable proteases derived from *Nocardiopsis* sp. NRRL 18262 (a 10R protease), as well as a protease derived from *Nocardiopsis alba* DSM 14010 in animal feed. WO 04/072221, WO 04/111220, WO 04/111223, WO 05/035747, and WO 05/123911 disclose proteases related to the 10R protease and their use in animal feed. WO 04/072279 discloses the use of other proteases in animal feed. WO 04/034776 discloses the use of a subtilisin/keratinase, PWD-1 from *B. Licheniformis*, in the feed of poultry. WO 04/077960 discloses a method for increasing the digestibility of forage or grain in ruminants by applying a bacterial or fungal protease.

Commercial products comprising a protease and marketed for use in animal feed include RONOZYME® ProAct (DSM NP/Novozymes), Axtra® (Danisco), Avizyme® (Danisco), Porzyme® (Danisco), Allzyme™ (Alltech), Versazyme® (BioResources, Int.), Poultrygrow™ (Jefo) and Cibenza® DP100 (Novus).

SUMMARY OF THE INVENTION

The present invention relates to isolated polypeptides having protease activity for use in animal feed selected from the group consisting of:

(a) a polypeptide having at least 80% sequence identity to the polypeptide of SEQ ID NO: 5;

(b) a polypeptide encoded by a polynucleotide that hybridizes under medium-high stringency conditions, high stringency conditions or very high stringency conditions with:

(i) the mature polypeptide coding sequence of SEQ ID NO: 1;

(ii) the mature polypeptide coding sequence of SEQ ID NO: 3; and/or (iii) the full-length complementary strand of (i) or (ii);

(c) a polypeptide encoded by a polynucleotide having at least 80% sequence identity to the mature polypeptide coding sequence of SEQ ID NO: 1 or SEQ ID NO: 3;

(d) a variant of the polypeptide of SEQ ID NO: 5 having at least 80% sequence identity to the polypeptide of SEQ ID NO: 5 comprising a substitution, deletion, and/or insertion at one or more (several) positions; and (e) a fragment of a polypeptide of (a), (b), (c) or (d) that has protease activity.

The present invention also relates to variant polypeptides having protease activity and having at least 80% sequence identity to the polypeptide of SEQ ID NO: 5, selected from the group consisting of:

(a) a variant of the polypeptide of SEQ ID NO: 5 comprising at least one substitution, deletion, and/or insertion at one or more (several) positions; and (b) a fragment of a polypeptide of (a) that has protease activity.

The present invention relates to isolated polynucleotides encoding the polypeptides of the present invention, nucleic acid constructs, recombinant expression vectors, and recombinant host cells comprising the polynucleotides, and to methods of producing the polypeptides.

The present invention also relates to compositions of the isolated polypeptide of the present invention, methods for preparing a composition for use in animal feed, improving the nutritional value of an animal feed, and methods of treating proteins to be used in animal feed compositions.

Overview of Sequence Listing

SEQ ID NO: 1 is the DNA sequence of S1 protease 2 as isolated from *Saccharopolyspora erythraea* (EMBL: AM420293).

SEQ ID NO: 2 is the amino acid sequence as deduced from SEQ ID NO: 1.

SEQ ID NO: 3 is the DNA sequence of the synthetically optimised gene fused with the Savinase signal peptide.

SEQ ID NO: 4 is the amino acid sequence as deduced from SEQ ID NO: 3.

SEQ ID NO: 5 is the amino acid sequence of the mature S1 protease 2 from *Saccharopolyspora erythraea*.

SEQ ID NO: 6 is the DNA sequence of protease 10R (WO 05/035747, SEQ ID NO: 1).

SEQ ID NO: 7 is the amino acid sequence of protease 10R (WO 05/035747, SEQ ID NO: 2).

SEQ ID NO: 8 is the amino acid sequence of the protease from *Saccharomonospora xinjiangensis* XJ-54 (Uniprot: I0V8H8).

SEQ ID NO: 9 is the amino acid sequence of an endopeptidase from *Saccharomonospora paurometabolica* YIM 90007 (Uniprot: G4J6Q2).

SEQ ID NO: 10 is the amino acid sequence of a Chymotrypsin-like protease from *Kribbella flavida* DSM 17836 (Uniprot: D2PRB9).

SEQ ID NO: 11 is the amino acid sequence of a serine protease from *Saccharomonospora viridis* (Uniprot: C7MV18).

SEQ ID NO: 12 is the amino acid sequence of a Streptogrisin C like protein *Saccharothrix espanaensis* DSM 44229T (Uniprot: K0JWC2).

SEQ ID NO: 13 is the amino acid sequence of a Streptogrisin C like protein *Saccharothrix espanaensis* DSM 44229T (Uniprot: K0JQQ4).

SEQ ID NO: 14 is the *Bacillus lentus* secretion signal.

Identity Matrix of Sequences

| | SEQ ID NO: 2 | SEQ ID NO: 4 | SEQ ID NO: 5 | SEQ ID NO: 7 | SEQ ID NO: 8 | SEQ ID NO: 9 | SEQ ID NO: 10 | SEQ ID NO: 11 | SEQ ID NO: 12 | SEQ ID NO: 13 |
|---|---|---|---|---|---|---|---|---|---|---|
| SEQ2 | 100 | 100 | 100 | 48.8 | 66.6 | 62.6 | 58.7 | 64.5 | 58.4 | 57.2 |
| SEQ4 | 100 | 100 | 100 | 48.8 | 66.6 | 62.6 | 58.7 | 64.5 | 58.4 | 57.2 |
| SEQ5 | 100 | 100 | 100 | 58.9 | 76.5 | 74.7 | 74.7 | 73.8 | 74.3 | 73.6 |
| SEQ7 | 48.8 | 48.8 | 58.9 | 100 | 49.7 | 48.5 | 47.8 | 50.0 | 48.5 | 43.6 |
| SEQ8 | 66.6 | 66.6 | 76.5 | 49.7 | 100 | 73.1 | 54.6 | 73.8 | 55.2 | 54.5 |
| SEQ9 | 62.6 | 62.6 | 74.7 | 48.5 | 73.1 | 100 | 53.4 | 70.1 | 55.2 | 52.0 |
| SEQ10 | 58.7 | 58.7 | 74.7 | 47.8 | 54.6 | 53.4 | 100 | 55.5 | 55.2 | 66.0 |
| SEQ11 | 64.5 | 64.5 | 73.8 | 50.0 | 73.8 | 70.1 | 55.5 | 100 | 55.8 | 52.9 |
| SEQ12 | 58.4 | 58.4 | 74.3 | 48.5 | 55.2 | 55.2 | 55.2 | 55.8 | 100 | 57.2 |
| SEQ13 | 57.2 | 57.2 | 73.6 | 43.6 | 54.5 | 52.0 | 66.0 | 52.9 | 57.2 | 100 |

DEFINITIONS

Figure 1:
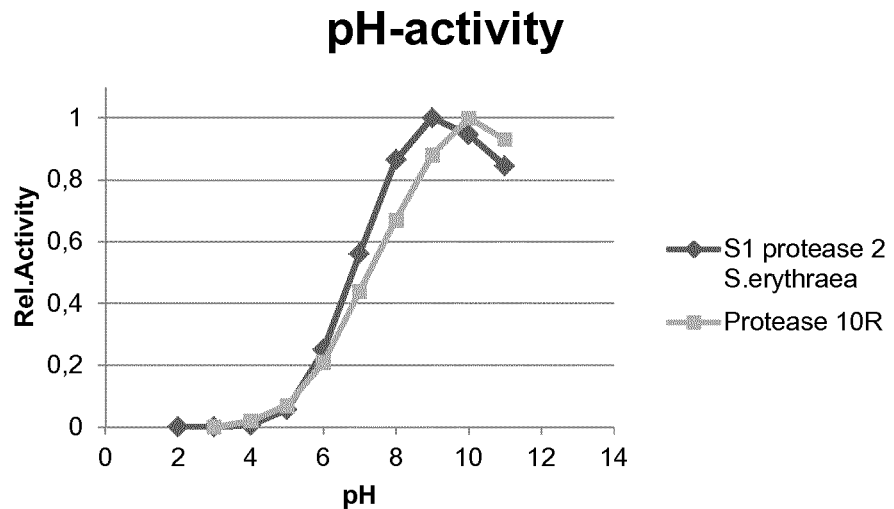
FIG. 1 shows the pH-activity profile of S1 protease 2 as isolated from *Saccharopolyspora erythraea* compared to protease 10R on the Suc-AAPF-pNA substrate at 37° C.
Figure 2:
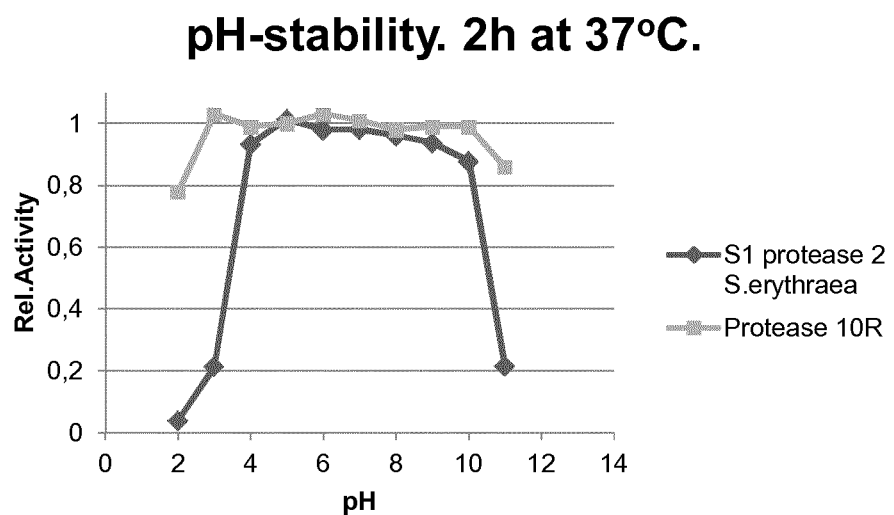
FIG. 2 shows the pH-stability profile of S1 protease 2 as isolated from *Saccharopolyspora erythraea* compared to protease 10R (residual activity after 2 hours at 37° C.).
Figure 3:
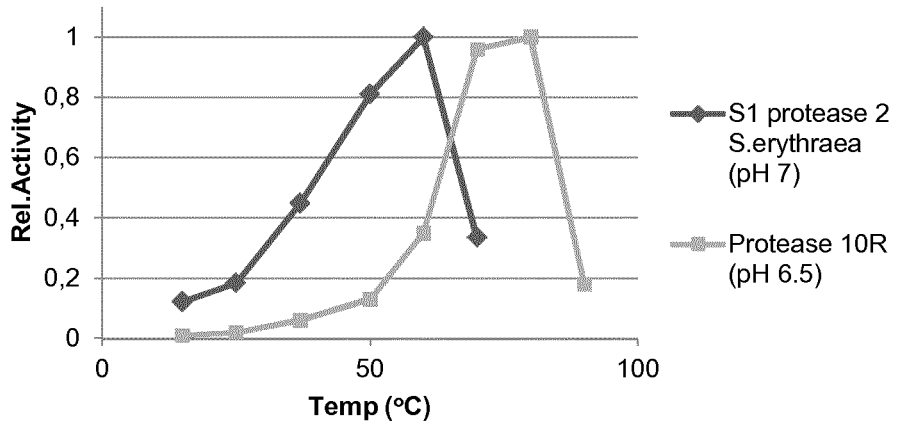
FIG. 3 shows the temperature activity profile of S1 protease 2 as isolated from *Saccharopolyspora erythraea* at pH 7.0 compared to protease 10R on Protazyme AK at pH 6.5.
Figure 4:
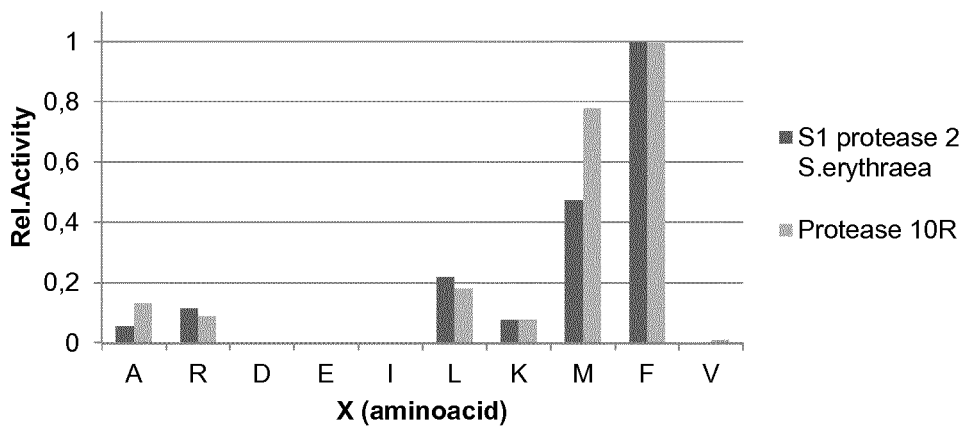
FIG. 4 shows the P1-specificity of S1 protease 2 as isolated from *Saccharopolyspora erythraea* compared to protease 10R on 10 Suc-AAPX-pNA substrates at pH 9.0, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Fragment: The term "fragment" means a polypeptide having one or more (several) amino acids deleted from the amino and/or carboxyl terminus of a mature polypeptide; wherein the fragment has protease activity. In one aspect, a fragment contains at least 163 amino acid residues (e.g., amino acids 11 to 173 of SEQ ID NO: 2), or at least 173 amino acid residues (e.g., amino acids 6 to 178 of SEQ ID NO: 2); or correspondingly for SEQ ID NO: 4 a fragment contains at least 163 amino acid residues (e.g., amino acids 11 to 173 of SEQ ID NO: 4), or at least 173 amino acid residues (e.g., amino acids 6 to 178 of SEQ ID NO: 4); or correspondingly for SEQ ID NO: 5 a fragment contains at least 163 amino acid residues (e.g., amino acids 11 to 173 of SEQ ID NO: 5), or at least 173 amino acid residues (e.g., amino acids 6 to 178 of SEQ ID NO: 5).

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Isolated polypeptide: The term "isolated polypeptide" means a polypeptide that is modified by the hand of man relative to that polypeptide as found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 183 of SEQ ID NO: 2 based on the SignalP (Nielsen et al., 1997, *Protein Engineering* 10: 1-6) prediction program that also predicts −194 to −154 of SEQ ID NO: 2 are a signal peptide. In another aspect, the mature polypeptide is amino acids 1 to 183 of SEQ ID NO: 4 based on sequencing using Edman degredation and intact molecular weight analysis. Amino acids −180 to −154 of SEQ ID NO: 4 is the Savinase signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having protease activity. In one aspect, the mature polypeptide coding sequence is nucleotides 683 to 1231 in the numbering of SEQ ID NO: 1 and nucleotides 541 to 1089 in the numbering of SEQ ID NO: 3 based on the determination of the mature polypeptide by Edman dedgrdation and intact molecular weight analysis. Furthermore nucleotides 101 to 223 in the numbering of SEQ ID NO: 1 are predicted to encode a signal peptide based on the prediction program SignalP (Nielsen et al., 1997, *Protein Engineering* 10: 1-6) and nucleotides 1 to 81 in the numbering of SEQ ID NO: 3 encode the Savinase signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide such that the control sequence directs the expression of the coding sequence.

Protease activity: The term "protease activity" means proteolytic activity (EC 3.4). Proteases of the invention are endopeptidases (EC 3.4.21). There are several protease activity types, although the three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

For the purpose of the present invention, protease activity was determined using assays which are described in "Materials and Methods", such as the Kinetic Suc-AAPF-pNA assay, Protazyme AK assay, Kinetic Suc-AAPX-pNA assay and o-Phthaldialdehyde (OPA). For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity.

The polypeptides of the present invention have at least 20%, e.g., at least 40%, at least 50%, at least 60%, at least 70%, at least 80%, at least 90%, at least 95%, and at least 100% of the protease activity of the polypeptide of SEQ ID NO: 5.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Stringency conditions: The different strigency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 489 nucleotides (e.g., nucleotides 713 to 1201 of SEQ ID NO: 1 or nucleotides 571 to 1059 of SEQ ID NO: 3). In another aspect, a subsequence contains at least 519 nucleotides (e.g., nucleotides 698 to 1216 of SEQ ID NO: 1 or nucleotides 556 to 1074 of SEQ ID NO: 3).

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having protease activity and having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to SEQ ID NO: 5, comprising an alteration, i.e., a substitution, insertion, and/or deletion of one or more (several) amino acid residues at one or more (several) positions. A substitution means a replacement of an amino acid occupying a position with a different amino acid; a deletion means removal of e.g. 1-5 amino acid residues occupying 1-5 positions; and an insertion means adding e.g. 1-5 amino acids adjacent to an amino acid occupying a position. The variants of the present invention have at least 20%, e.g., at least 40%, at least 50%, at least 60%, at least 70%, at least 80%, at least 90%, at least 95%, or at least 100% of the protease activity of the polypeptide of SEQ ID NO: 5. A variant may also be a naturally occurring protease having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 5.

DETAILED DESCRIPTION OF THE INVENTION

Polypeptides Having Protease Activity

Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the eighteen subclasses thereof). The EC number refers to Enzyme Nomenclature 1992 from NC-IUBMB, Academic Press, San Diego, Calif., including supplements 1-5 published in 1994, *Eur. J. Biochem.* 223: 1-5; 1995, *Eur. J. Biochem.* 232: 1-6; 1996, *Eur. J. Biochem.* 237: 1-5; 1997, *Eur. J. Biochem.* 250: 1-6; and 1999, *Eur. J. Biochem.* 264: 610-650 respectively. The nomenclature is regularly supplemented and updated; see e.g. the World Wide Web (WWW) at www.chem.qmw.ac.uk/iubmb/enzyme/index.html.

The present invention provides for the use of polypeptides having protease activity in animal feed compositions. It also provides polynucleotides encoding the polypeptides. The proteases of the invention are serine proteases of the peptidase family S1. The proteases of the invention exhibit surprising pH properties, which makes them interesting candidates for use in animal feed. The proteases of the invention are thus most active on Suc-Ala-Ala-Pro-Phe-pNA but have reasomable activity on Suc-Ala-Ala-Pro-Met-pNA within a broad pH range of 5-11 and exhibit especially high activity in the pH range of 6-11. They are active on a feed relevant soybean meal-maize meal substrate within a broad physiological pH range of pH 3-7 and retain more than 90% activity after being subjected for 2 hours to a pH as low as 4.

The proteases of the invention and for use according to the invention are selected from the group consisting of:

(a) proteases belonging to the EC 3.4.21. enzyme group; and/or (b) Serine proteases of the peptidase family S1;

as described in 1993, *Biochem. J.* 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233.

For determining whether a given protease is a serine protease, and a family S1 protease, reference is made to the above Handbook and the principles indicated therein. Such determination can be carried out for all types of proteases, be it naturally occurring or wild-type proteases; or genetically engineered or synthetic proteases.

Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1.

The peptidases of family S1 contain the catalytic triad in the order His, Asp, Ser. Mutation of any of the amino acids of the catalytic triad will result in change or loss of enzyme activity. The amino acids of the catalytic triad of the S1 protease 2 as isolated from *Saccharpolyspora erythraea* (SEQ ID NO: 5) are probably positions His-32, Asp-56 and Ser-137.

The polypeptides of the present invention have at least 20%, e.g., at least 40%, at least 50%, at least 60%, at least 70%, at least 80%, at least 90%, at least 95%, at least 96%, at least 97%, at least 98%, at least 99%, and at least 100% of the protease activity of the mature polypeptide of SEQ ID NO: 5.

The present invention provides polypeptides having protease activity and polynucleotides encoding the polypeptides. The proteases of the invention are serine proteases of the peptidase family S1. The proteases of the invention exhibit pH properties, especially pH stability properties which make them of substantial interest as candidates for use in animal feed and other applications.

The present invention relates to the use of isolated polypeptides having protease activity in animal feed selected from the group consisting of:
(a) a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 5;
(b) a polypeptide encoded by a polynucleotide that hybridizes under medium-high stringency conditions, high stringency conditions, or very high stringency conditions with:
   (i) the mature polypeptide coding sequence of SEQ ID NO: 1;
   (ii) the mature polypeptide coding sequence of SEQ ID NO: 3;
   (iii) the full-length complementary strand of (i) or (ii);
(c) a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or SEQ ID NO: 3;
(d) a variant of the polypeptide of SEQ ID NO: 5 having at least 80% sequence identity to the polypeptide of SEQ ID NO: 5 comprising a substitution, deletion, and/or insertion at one or more (several) positions; and
(e) a fragment of a polypeptide of (a), (b), (c) or (d) that has protease activity.

The present invention relates to the use in animal feed isolated polypeptides having a sequence identity to the mature polypeptide of SEQ ID NO: 2 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than thirtysix amino acids, e.g., by thirty amino acids, by twentyfive amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 2.

The present invention also relates to the use in animal feed of isolated polypeptides having a sequence identity to the mature polypeptide of SEQ ID NO: 4 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no than thirtysix amino acids, e.g., by thirty amino acids, by twentyfive amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 4.

The present invention further relates to the use in animal feed of isolated polypeptides having a sequence identity to the polypeptide of SEQ ID NO: 5 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than thirtysix amino acids, e.g., by thirty amino acids, by twentyfive amino acids, by twenty amino acids, by fifteen amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 5.

An embodiment of the invention is a polypeptide or a polypeptide encoded by a polynucleotide for use in animal feed having at least 85% sequence identity to the polypeptide of SEQ ID NO: 5.

An embodiment of the invention is a polypeptide or a polypeptide encoded by a polynucleotide for use in animal feed having at least 86% sequence identity to the polypeptide of SEQ ID NO: 5.

An embodiment of the invention is a polypeptide or a polypeptide encoded by a polynucleotide for use in animal feed having at least 87% sequence identity to the polypeptide of SEQ ID NO: 5.

An embodiment of the invention is a polypeptide or a polypeptide encoded by a polynucleotide for use in animal feed having at least 88% sequence identity to the polypeptide of SEQ ID NO: 5.

An embodiment of the invention is a polypeptide or a polypeptide encoded by a polynucleotide for use in animal feed having at least 89% sequence identity to the polypeptide of SEQ ID NO: 5.

An embodiment of the invention is a polypeptide or a polypeptide encoded by a polynucleotide for use in animal feed having at least 90% sequence identity to the polypeptide of SEQ ID NO: 5.

An embodiment of the invention is a polypeptide or a polypeptide encoded by a polynucleotide for use in animal feed having at least 91% sequence identity to the polypeptide of SEQ ID NO: 5.

An embodiment of the invention is a polypeptide or a polypeptide encoded by a polynucleotide for use in animal feed having at least 92% sequence identity to the polypeptide of SEQ ID NO: 5.

An embodiment of the invention is a polypeptide or a polypeptide encoded by a polynucleotide for use in animal feed having at least 93% sequence identity to the polypeptide of SEQ ID NO: 5.

An embodiment of the invention is a polypeptide or a polypeptide encoded by a polynucleotide for use in animal feed having at least 94% sequence identity to the polypeptide of SEQ ID NO: 5.

An embodiment of the invention is a polypeptide or a polypeptide encoded by a polynucleotide for use in animal feed having at least 95% sequence identity to the polypeptide of SEQ ID NO: 5.

An embodiment of the invention is a polypeptide or a polypeptide encoded by a polynucleotide for use in animal feed having at least 96% sequence identity to the polypeptide of SEQ ID NO: 5.

An embodiment of the invention is a polypeptide or a polypeptide encoded by a polynucleotide for use in animal feed having at least 97% sequence identity to the polypeptide of SEQ ID NO: 5.

An embodiment of the invention is a polypeptide or a polypeptide encoded by a polynucleotide for use in animal feed having at least 98% sequence identity to the polypeptide of SEQ ID NO: 5.

An embodiment of the invention is a polypeptide or a polypeptide encoded by a polynucleotide for use in animal feed having at least 99% sequence identity to the polypeptide of SEQ ID NO: 5.

An embodiment of the invention is a polypeptide or a polypeptide encoded by a polynucleotide for use in animal feed having 100% sequence identity to the polypeptide of SEQ ID NO: 5.

The present invention also relates to isolated polypeptides having protease activity and having at least 80% sequence identity to the polypeptide of SEQ ID NO: 5, selected from the group consisting of:

(a) a variant of the polypeptide of SEQ ID NO: 5 comprising a substitution, deletion, and/or insertion at one or more (several) positions; and (b) a fragment of a polypeptide of (a) that has protease activity.

An embodiment of the invention is a polypeptide or a polypeptide encoded by a polynucleotide having at least 85% sequence identity to the polypeptide of SEQ ID NO: 5.

An embodiment of the invention is a polypeptide or a polypeptide encoded by a polynucleotide having at least 86% sequence identity to the polypeptide of SEQ ID NO: 5.

An embodiment of the invention is a polypeptide or a polypeptide encoded by a polynucleotide having at least 87% sequence identity to the polypeptide of SEQ ID NO: 5.

An embodiment of the invention is a polypeptide or a polypeptide encoded by a polynucleotide having at least 88% sequence identity to the polypeptide of SEQ ID NO: 5.

An embodiment of the invention is a polypeptide or a polypeptide encoded by a polynucleotide having at least 89% sequence identity to the polypeptide of SEQ ID NO: 5.

An embodiment of the invention is a polypeptide or a polypeptide encoded by a polynucleotide having at least 90% sequence identity to the polypeptide of SEQ ID NO: 5.

An embodiment of the invention is a polypeptide or a polypeptide encoded by a polynucleotide having at least 91% sequence identity to the polypeptide of SEQ ID NO: 5.

An embodiment of the invention is a polypeptide or a polypeptide encoded by a polynucleotide having at least 92% sequence identity to the polypeptide of SEQ ID NO: 5.

An embodiment of the invention is a polypeptide or a polypeptide encoded by a polynucleotide having at least 93% sequence identity to the polypeptide of SEQ ID NO: 5.

An embodiment of the invention is a polypeptide or a polypeptide encoded by a polynucleotide having at least 94% sequence identity to the polypeptide of SEQ ID NO: 5.

An embodiment of the invention is a polypeptide or a polypeptide encoded by a polynucleotide having at least 95% sequence identity to the polypeptide of SEQ ID NO: 5.

An embodiment of the invention is a polypeptide or a polypeptide encoded by a polynucleotide having at least 96% sequence identity to the polypeptide of SEQ ID NO: 5.

An embodiment of the invention is a polypeptide or a polypeptide encoded by a polynucleotide having at least 97% sequence identity to the polypeptide of SEQ ID NO: 5.

An embodiment of the invention is a polypeptide or a polypeptide encoded by a polynucleotide having at least 98% sequence identity to the polypeptide of SEQ ID NO: 5.

An embodiment of the invention is a polypeptide or a polypeptide encoded by a polynucleotide having at least 99% sequence identity to the polypeptide of SEQ ID NO: 5.

A polypeptide of the present invention preferably comprises or consists of the amino acid sequence of SEQ ID NO: 2, SEQ ID NO: 4 or SEQ ID NO: 5, an allelic variant thereof; or is a fragment missing e.g. 30, 25, 20, 15, 10 or 5 amino acids from the N- and/or C-terminal and having protease activity. In another aspect, the polypeptide comprises or consists of the polypeptide of SEQ ID NO: 2, SEQ ID NO: 4 and/or SEQ ID NO: 5. In another preferred aspect, the polypeptide comprises or consists of amino acids 1 to 193 of SEQ ID NO: 2, amino acids 1 to 193 of SEQ ID NO: 4, and/or amino acids 1 to 193 of SEQ ID NO: 5.

The present invention also relates to isolated polypeptides having protease activity that are encoded by polynucleotides that hybridize under medium-high stringency conditions, high stringency conditions, or very high stringency conditions with (i) the mature polypeptide coding sequence of SEQ ID NO: 1, (ii) the mature polypeptide coding sequence of SEQ ID NO: 3, or (iii) the full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1, SEQ ID NO: 3 or a subsequence thereof, as well as the amino acid sequence of SEQ ID NO: 2, SEQ ID NO: 4 or SEQ ID NO: 5, or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, SEQ ID NO: 3 or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1, the mature polypeptide coding sequence of SEQ ID NO: 3; its full-length complementary strand; or a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1 or SEQ ID NO: 3. In another aspect, the nucleic acid probe is a fragment thereof. In another aspect, the nucleic acid probe is a polynucleotide that encodes the polypeptide of SEQ ID NO: 2, SEQ ID NO: 4, SEQ ID NO: 5 or a fragment thereof. In another preferred aspect, the nucleic acid probe is SEQ ID NO: 1 or SEQ ID NO: 3.

For long probes of at least 100 nucleotides in length, high to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, Proc. Natl. Acad. Sci. USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

The present invention also relates to the use in animal feed of isolated polypeptides having protease activity encoded by polynucleotides having a sequence identity to the mature polypeptide coding sequence of SEQ ID NO: 1 of at least least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The present invention also relates to variant polypeptides having protease activity and having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the polypeptide of SEQ ID NO: 5 comprising at least one substitution, deletion, and/or insertion of at least one or more (several) amino acids of SEQ ID NO: 5 or a homologous sequence thereof.

The variant polypeptide of the invention may in one embodiment have at least 86% sequence identity to SEQ ID NO: 5.

The variant polypeptide of the invention may in one embodiment have at least 87% sequence identity to SEQ ID NO: 5.

The variant polypeptide of the invention may in one embodiment have at least 88% sequence identity to SEQ ID NO: 5.

The variant polypeptide of the invention may in one embodiment have at least 89% sequence identity to SEQ ID NO: 5.

The variant polypeptide of the invention may in one embodiment have at least 90% sequence identity to SEQ ID NO: 5.

The variant polypeptide of the invention may in one embodiment have at least 91% sequence identity to SEQ ID NO: 5.

The variant polypeptide of the invention may in one embodiment have at least 92% sequence identity to SEQ ID NO: 5.

The variant polypeptide of the invention may in one embodiment have at least 93% sequence identity to SEQ ID NO: 5.

The variant polypeptide of the invention may in one embodiment have at least 94% sequence identity to SEQ ID NO: 5.

The variant polypeptide of the invention may in one embodiment have at least 95% sequence identity to SEQ ID NO: 5.

The variant polypeptide of the invention may in one embodiment have at least 96% sequence identity to SEQ ID NO: 5.

The variant polypeptide of the invention may in one embodiment have at least 97% sequence identity to SEQ ID NO: 5.

The variant polypeptide of the invention may in one embodiment have at least 98% sequence identity to SEQ ID NO: 5.

The variant polypeptide of the invention may in one embodiment have at least 99% sequence identity to SEQ ID NO: 5.

In a further embodiment, the total number of positions of the variant polypeptide of the invention (SEQ ID NO: 5) having amino acid substitutions, deletions and/or insertions is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

The present invention also relates to the use in animal feed of isolated polypeptides having protease activity encoded by polynucleotides having a sequence identity to the mature polypeptide coding sequence of SEQ ID NO: 3 of at least least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%

In another embodiment, the present invention also relates to variants for use in animal feed comprising a substitution, deletion, and/or insertion of one or more (or several) amino acids of SEQ ID NO: 2 or a homologous sequence thereof.

The total number of positions having amino acid substitutions, deletions and/or insertions in SEQ ID NO: 2 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In another embodiment, the present invention also relates to variants for use in animal feed comprising a substitution, deletion, and/or insertion of one or more (or several) amino acids of SEQ ID NO: 4 or a homologous sequence thereof. The total number of positions having amino acid substitutions, deletions and/or insertions in SEQ ID NO: 4 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

In another embodiment, the present invention also relates to variants for use in animal feed comprising a substitution, deletion, and/or insertion of one or more (or several) amino acids of SEQ ID NO: 5 or a homologous sequence thereof. The total number of positions having amino acid substitutions, deletions and/or insertions in SEQ ID NO: 5 is not more than 36, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36. The amino acid changes may be of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges that are expected not to alter the specific activity substantially are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be hybrid polypeptide in which a portion of one polypeptide is fused at the N-terminus or the C-terminus of a portion of another polypeptide.

The polypeptide may be a fusion polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol.

76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Embodiments

In certain embodiments of the invention, the protease of the invention exhibits beneficial thermal properties such as thermostability, steam stability, etc and/or pH properties, such as acid stability, pH optimum, etc.

An embodiment of the invention is isolated polypeptides for use in animal feed having improved protease activity between pH 6 and 9, at 37° C. compared to protease 10R.

A further embodiment of the invention is isolated polypeptides for use in animal feed having improved protease activity between 15° C. and 60° C., such as between 25° C. and 50° C., or at 15° C., at 25° C., at 37° C., at 50° C. or at 60° C. compared to protease 10R.

An additional embodiment of the invention is isolated polypeptides for use in animal feed having improved protease activity on soybean-maze meal between pH 3.0 and 5.0, such as at pH 3.0, 4.0 or 5.0 at 40° C. compared to protease 10R.

Acidity/Alkalinity Properties

In certain embodiments of the invention the protease of the invention exhibits beneficial properties in respect of pH, such as acid stability, pH optimum, etc. Stability of the protease at a low pH is beneficial since the protease can have activity in the intestine after passing through the stomach. In one embodiment of the invention the protease retains >90% activity after 2 hours at pH 4 as determined using the method described in Example 3.

Temperature-Activity

The temperature-activity profile of the protease may be determined as described in Example 3. Activity at low temperatures (30-40° C.) can be advantageous for the digestion of proteins in an animal.

In one embodiment, the invention comprises of a protease having a temperature activity profile at pH 7.0 with relative activity of 0.15 or higher at 25° C., or relative activity of 0.40 or higher at 37° C., or relative activity of 0.75 or higher at 50° C. when compared to the activity of the protease at 60° C. (cf. Example 3).

pH-Activity

The pH-activity profile of the protease may be determined as described in Example 3. Activity at pH 6-8 can be advantageous for the digestion of proteins in the intestine of an animal.

In one embodiment, the invention comprises of a protease for use in animal feed having a pH-activity profile at 37° C. with relative activity of 0.50 or higher at pH 7, or relative activity of 0.80 or higher at pH 8 when compared to the activity of the protease at pH 9 (cf. Example 3).

Thermostability

Thermostability may be determined as described in Example 5, i.e. using DSC measurements to determine the denaturation temperature, $T_d$, of the purified protease protein. The Td is indicative of the thermostability of the protein: The higher the $T_d$, the higher the thermostability. Accordingly, in a preferred embodiment, the protease of the invention has a $T_d$ which is higher than the $T_d$ of a reference protease, wherein $T_d$ is determined on purified protease samples (preferably with a purity of at least 90% or 95%, as determined by SDS-PAGE).

In preferred embodiments, the thermal properties such as heat-stability, temperature stability, thermostability, steam stability, and/or pelleting stability as provided by the residual activity, denaturation temperature $T_d$, or other parameter of the protease of the invention is higher than the corresponding value, such as the residual activity or $T_d$, of the protease of SEQ ID NO: 5, more preferably at least 101% thereof, or at least 102%, 103%, 104%, 105%, 106%, 107%, 108%, 109%, or at least 110% thereof. Even more preferably, the value of the parameter, such as residual activity or $T_d$, of the protease of the invention is at least 120%, 130%, 140%, 150%, 160%, 170%, 180%, or at least 190% of the value for the protease of SEQ ID NO: 5.

In still further particular embodiments, the thermostable protease of the invention has a melting temperature, $T_m$ (or a denaturation temperature, $T_d$), as determined using Differential Scanning calorimetry (DSC) as described in example 10 (i.e. in 20 mM sodium acetate, pH 4.0), of at least 50° C. In still further particular embodiments, the $T_m$ is at least 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C.

Steam Stability

Steam stability may be determined as described in Example 6 by determining the residual activity of protease molecules after steam treatment at 85° C. or 90° C. for a short time.

Pelleting Stability

Pelleting stability may be determined as described in Example 7 by using enzyme granulate pre-mixed with feed. From the mixer the feed is conditioned with steam to 95° C. After conditioning the feed is pressed to pellets and the residual activity determined.

Sources of Polypeptides Having Protease Activity

A polypeptide having protease activity and to be used according to the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a polypeptide having protease activity from a gram-positive bacterium within a phylum such Actinobacteria or from a gram-negative bacterium within a phylum such as Proteobacteria.

In one aspect, the polypeptide is a protease from a bacterium of the class Actinobacteria, such as from the order Actinomycetales, or from the suborder Pseudonocardineae, or from the family Pseudonocardiaceae, or from the genus *Saccharopolyspora*, or from the species *Saccharopolyspora erythraea*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these taxa are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polynucleotides

The present invention also relates to isolated polynucleotides encoding a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* sp., or another or related organism from the order Bacillales and thus, for example, may be an allelic or species variant of the polypeptide encoding region of the polynucleotide.

The present invention also relates to isolated polynucleotides comprising or consisting of polynucleotides having a degree of sequence identity to the mature polypeptide coding sequence of SEQ ID NO: 1 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, with the proviso that it is not 100% identical to the mature polypeptide coding sequence of SEQ ID NO: 1, and which encode a polypeptide having protease activity.

The present invention further relates to isolated polynucleotides comprising or consisting of polynucleotides having a degree of sequence identity to the mature polypeptide coding sequence of SEQ ID NO: 3 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1 or SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under medium-high stringency conditions, high stringency conditions, or very high stringency conditions with (i) the mature polypeptide coding sequence of SEQ ID NO: 1, (ii) the mature polypeptide coding sequence of SEQ ID NO: 3, (iii) the genomic DNA sequence comprising the mature polypeptide coding sequence of SEQ ID NO: 1, (iv) the genomic DNA sequence comprising the mature polypeptide coding sequence of SEQ ID NO: 3, or (v) the full-length complementary strand of (i), (ii), (iii), or (iv); or allelic variants and subsequences thereof (Sambrook et al., 1989, supra), as defined herein.

In one aspect, the polynucleotide comprises or consists of SEQ ID NO: 3, the mature polypeptide coding sequence of SEQ ID NO: 3, a subsequence of SEQ ID NO: 1 that encodes a fragment of SEQ ID NO: 2, SEQ ID NO: 4 or SEQ ID NO: 5 having protease activity, or a subsequence of SEQ ID NO: 3 that encodes a fragment of SEQ ID NO: 2, SEQ ID NO: 4 or SEQ ID NO: 5 having protease activity, such as the polynucleotide of nucleotides 541 to 1089 of SEQ ID NO: 3.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in *Aspergilli* in which the untranslated leader has been replaced by an untranslated leader from a gene encoding triose phosphate isomerase in *Aspergilli*; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Geobacillus stearothermophilus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. Specifically preferred host cells are *Bacillus subtilis* and *Bacillus licheniformis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios* 68: 189-207), by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii,*

*Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Bacillus*. In a more preferred aspect, the cell is *Bacillus* sp-19138.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

More details are provided in the Section on "Nucleic Acid Constructs, Expression Vectors, Recombinant Host Cells, and Methods for Production of Proteases" below.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Plants

The present invention also relates to plants, e.g., a transgenic plant, plant part, or plant cell, comprising an isolated polynucleotide of the present invention so as to express and produce the polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide may be constructed in accordance with methods known in the art. In short, the plant or plant cell is constructed by incorporating one or more (several) expression constructs encoding a polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct prepared according to the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. Crossing results in the introduction of a transgene into a plant line by cross pollinating a starting line with a donor plant line. Non-limiting examples of such steps are further articulated in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising: (a) cultivating a transgenic plant or a plant cell comprising a polynucleotide encoding the polypeptide under conditions conducive for production of the polypeptide; and (b) recovering the polypeptide.

Compositions

The present invention also relates to compositions comprising a protease of the present invention. Preferably, the compositions are enriched in such a protease. The term "enriched" indicates that the protease activity of the composition has been increased, e.g., with an enrichment factor of at least 1.1.

The composition may comprise a protease of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by microorganisms such as bacteria or fungi or by plants or by animals. The compositions may be prepared in accordance with methods known in the art and may be in the form of a liquid or a dry composition. For instance, the composition may be in the form of a granulate or a microgranulate. The protease may be stabilized in accordance with methods known in the art.

Uses

The present invention is also directed to methods for using the polypeptides having protease activity, or compositions thereof, for e.g. animal feed.

Animal Feed

The present invention is also directed to methods for using the proteases having protease activity in animal feed, as well as to feed compositions and feed additives comprising the proteases of the invention.

The term animal includes all animals, including human beings. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method.

A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may e.g. include other enzymes, in which case it could be termed a protease preparation.

The protease preparation can be (a) added directly to the feed (or used directly in a protein treatment process), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods.

Such protease preparation may of course be mixed with other enzymes.

The protein may be an animal protein, such as meat and bone meal, feather meal, and/or fish meal; or it may be a vegetable protein.

The term vegetable proteins as used herein refers to any compound, composition, preparation or mixture that includes at least one protein derived from or originating from a vegetable, including modified proteins and proteinderivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In a particular embodiment of a treatment process the protease(s) in question is affecting (or acting on, or exerting its hydrolyzing or degrading influence on) the proteins, such as vegetable proteins or protein sources. To achieve this, the protein or protein source is typically suspended in a solvent, eg an aqueous solvent such as water, and the pH and temperature values are adjusted paying due regard to the characteristics of the enzyme in question. For example, the treatment may take place at a pH-value at which the activity of the actual protease is at least 5%, 10%, 20%, 30%, 40%, 50%, 60%, 70%, 80%, or at least 90%. Likewise, for example, the treatment may take place at a temperature at which the activity of the actual protease is at least 5%, 10%, 20%, 30%, 40%, 50%, 60%, 70%, 80%, or at least 90%. The above percentage activity indications are relative to the maximum activities. The enzymatic reaction is continued until the desired result is achieved, following which it may or may not be stopped by inactivating the enzyme, e.g. by a heat-treatment step.

In another particular embodiment of a treatment process of the invention, the protease action is sustained, meaning e.g. that the protease is added to the proteins, but its hydrolysing influence is so to speak not switched on until later when desired, once suitable hydrolysing conditions are established, or once any enzyme inhibitors are inactivated, or whatever other means could have been applied to postpone the action of the enzyme.

In one embodiment the treatment is a pre-treatment of animal feed or proteins for use in animal feed, i.e. the proteins are hydrolysed before intake.

The term improving the nutritional value of an animal feed means improving the availability of nutrients in the feed. In this invention improving the nutritional values refers in particular to improving the availability of the protein fraction of the feed, thereby leading to increased protein extraction, higher protein yields, and/or improved protein utilization. When the nutritional value of the feed is increased, the protein and/or amino acid digestibility is increased and the growth rate and/or weight gain and/or feed conversion (i.e. the weight of ingested feed relative to weight gain) of the animal might be improved.

The protease can be added to the feed in any form, be it as a relatively pure protease or in admixture with other components intended for addition to animal feed, i.e. in the form of animal feed additives, such as the so-called premixes for animal feed.

In a further aspect the present invention relates to compositions for use in animal feed, such as animal feed, and animal feed additives, e.g. premixes.

Apart from the protease of the invention, the animal feed additives of the invention contain at least one fat-soluble vitamin, and/or at least one water soluble vitamin, and/or at least one trace mineral, and/or at least one macro mineral.

Further, optional, feed-additive ingredients are colouring agents, e.g. carotenoids such as beta-carotene, astaxanthin, and lutein; stabilisers; growth improving additives and aroma compounds/flavorings, e.g. creosol, anethol, deca-, undeca- and/or dodeca-lactones, ionones, irone, gingerol, piperidine, propylidene phatalide, butylidene phatalide, capsaicin and/or tannin; antimicrobial peptides; polyunsaturated fatty acids (PUFAs); reactive oxygen generating species; also, a support may be used that may contain, for example, 40-50% by weight of wood fibres, 8-10% by weight of stearine, 4-5% by weight of *curcuma* powder, 4-58% by weight of rosemary powder, 22-28% by weight of limestone, 1-3% by weight of a gum, such as gum arabic, 5-50% by weight of sugar and/or starch and 5-15% by weight of water.

A feed or a feed additive of the invention may also comprise at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); further protease (EC 3.4), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthethase.

Usually fat- and water-soluble vitamins, as well as trace minerals form part of a so-called premix intended for addition to the feed, whereas macro minerals are usually separately added to the feed. Either of these composition types, when enriched with a protease of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Destillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can e.g. be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) protease/enzyme preparation may also be added before or during the feed ingredient step. Typically a liquid protease/enzyme preparation is added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease should of course be applied in an effective amount, i.e. in an amount adequate for improving hydrolysis, digestibility, and/or improving nutritional value of feed.

It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease protein per kg feed (ppm).

For determining mg protease protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg protease protein per kg feed is calculated.

The same principles apply for determining mg protease protein in feed additives. Of course, if a sample is available of the protease used for preparing the feed additive or the feed, the specific activity is determined from this sample (no need to purify the protease from the feed composition or the additive).

Nucleic Acid Constructs, Expression Vectors, Recombinant Host Cells, and Methods for Production of Proteases The present invention also relates to nucleic acid constructs, expression vectors and recombinant host cells comprising such polynucleotides encoding the proteases of the invention.

The present invention also relates to methods of producing a protease, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides and fused polypeptides.

Preferably, the protein is a protease. For example, the protein may be a hydrolase, such as a proteolytic enzyme or protease. The gene may be obtained from any prokaryotic, eukaryotic, or other source.

The present invention is further described by the following examples that should not be construed as limiting the scope of the invention.

EXAMPLES

Materials and Methods
Protease Assays
1) Suc-AAPF-pNA Assay
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.
20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.
2) Protazyme AK Assay
Substrate: Protazyme AK tablet (cross-linked and dyed casein; from Megazyme)
Temperature: controlled (assay temperature).
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 6.5, 7.0, 8.0, 9.0, 10.0, and 11.0 with HCl or NaOH.
A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. $OD_{650}$ was read as a measure of protease activity. A buffer blind was included in the assay (instead of enzyme).
3) Suc-AAPX-pNA Assay
pNA substrates: Suc-AAPA-pNA (Bachem L-1775)
Suc-AAPR-pNA (Bachem L-1720)
Suc-AAPD-pNA (Bachem L-1835)
Suc-AAPI-pNA (Bachem L-1790)
Suc-AAPM-pNA (Bachem L-1395)
Suc-AAPV-pNA (Bachem L-1770)
Suc-AAPL-pNA (Bachem L-1390)
Suc-AAPE-pNA (Bachem L-1710)
Suc-AAPK-pNA (Bachem L-1725)
Suc-AAPF-pNA (Bachem L-1400)
Temperature: Room temperature (25° C.)
Assay buffer: 100 mM succinic acid, 100 mM HEPES, 100 mM CHES, 100 mM CABS, 1 mM $CaCl_2$, 150 mM KCl, 0.01% Triton X-100, pH 6.0 or pH 9.0.
20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.
o-Phthaldialdehyde (OPA) Assay
This assay detects primary amines and hence cleavage of peptide bonds by a protease can be measured as the difference in absorbance between a protease treated sample and a control sample. The assay is conducted essentially according to Nielsen et al. (Nielsen, P M, Petersen, D, Dampmann, C. Improved method for determining food protein degree of hydrolysis, 2001, *J Food Sci*, 66: 642-646).
500 µl of sample is filtered through a 100 kDa Microcon centrifugal filter (60 min, 11,000 rpm, 5° C.). The samples are diluted appropriately (e.g. 10, 50 or 100 times) in deionizer water and 25 µl of each sample is loaded into a 96 well microtiter plate (5 replicates). 200 µl OPA reagent (100 mM di-sodium tetraborate decahydrate, 3.5 mM sodium dodecyl sulphate (SDS), 5.7 mM di-thiothreitol (DDT), 6 mM o-phthaldialdehyde) is dispensed into all wells, the plate is shaken (10 sec, 750 rpm) and absorbance measured at 340 nm.
Strain
The nucleotide sequence encoding the S1 protease 1 from *Saccharopolyspora erythraea* was published by Oliynyk et al in 'Complete genome sequence of the erythromycin-producing bacterium *Saccharopolyspora erythraea* NRRL23338', 2007, Nat. Biotechnol. 25:447-453 and the gene was submitted to EMBL/GenBank under accession number EMBL: AM420293. According to Oliynyk, 'the strain used, NRRL23338, is the original form of the type strain of *S. erythraca* NRRL2338, which is now listed as NRRL23338 white in the NRRL database'. The NRRL database indicates (under NRRL number B-24071 which corresponds to NRRL 23338 white) that the 'white colony variant was isolated from growth from ampule from second lyophilization'. The reference for NRRL2338 refers to U.S. Pat. No. 2,653,899 wherein it is stated that the original sample of *S. erythraca* NRRL2338 was obtained as a soil sample from Ilonio City, Phillipine Islands on or before 1952.

Example 1

Expression of the S1 Protease 2 from *Saccharopolyspora erythraea*

Based on the published nucleotide sequence identified as SEQ ID NO: 1, a synthetic gene having SEQ ID NO: 3 was synthesized by Gene Art (GENEART AG BioPark, Josef-Engert-Str. 11, 93053, Regensburg, Germany). The synthetic gene was subcloned using ClaI and MluI restriction sites into a *Bacillus* expression vector as described in WO 12/025577. Transformants were selected on LB plates supplemented with 6 µg of chloramphenicol per ml. The recombinant *Bacillus subtilis* clone containing the integrated expression construct was selected and designated as S1 protease 2 from *Saccharopolyspora erythraea*. It was cultivated on a rotary shaking table in 500 mL baffled Erlenmeyer flasks each containing 100 ml casein-based media supplemented with 34 mg/l chloramphenicol. The clone was cultivated for 5 days at 26° C., at 225 rpm. The enzyme containing supernatants were harvested and the enzyme purified as described in Example 2.

Example 2

Purification of the S1 Protease 2 from *Saccharopolyspora erythraea*

The culture broth was centrifuged (20000×g, 20 min) and the supernatant was carefully decanted from the precipitate. The supernatant was filtered through a Nalgene 0.2 µm filtration unit in order to remove the rest of the *Bacillus* host cells. The 0.2 µm filtrate was transferred to 20 mM Tris/HCl, 1 mM $CaCl_2$, pH 8.0 on a G25 sephadex column (from GE Healthcare). The G25 sephadex transferred filtrate was applied to a Q-sepharose FF column (from GE Healthcare) equilibrated in 20 mM Tris/HCl, 1 mM $CaCl_2$, pH 8.0. After washing the column with the equilibration buffer, the protease was eluted with a linear NaCl gradient (0→0.5M) in the same buffer over five column volumes. Fractions from the column were analysed for protease activity (using the Suc-AAPF-pNA assay at pH 9) and peak-fractions were pooled. Solid $(NH_4)_2SO_4$ was added to the pool from the Q-sepharose FF column to a final 2.0M $(NH_4)_2SO_4$ concentration and the salt adjusted pool was applied to a Phenyl-Toyopearl column (from TosoHaas) equilibrated in 100 mM $H_3BO_3$, 10 mM MES, 2 mM $CaCl_2$, 2.0M $(NH_4)_2SO_4$, pH 6.0. After washing the column with the equilibration buffer, the protease was eluted with a linear $(NH_4)_2SO_4$ gradient (2.0→0M) in the same buffer over five column volumes. Fractions from the column were analysed for protease activity (using the Suc-AAPF-pNA assay at pH 9) and peak-fractions were pooled. The pool from the Phenyl-Toyopearl column was diluted 3 times with 50 mM Citric acid/NaOH, 1 mM $CaCl_2$, pH 4.0 and the pH was adjusted to pH 4.0 with 1M HCl. The adjusted pool was applied to an XpressLine ProA column (from UpFront chromatography) equilibrated in 50 mM Citric acid/NaOH, 1 mM $CaCl_2$, pH 4.0. After washing the column extensively with the equilibration buffer, the protease was step-eluted with 50 mM Tris/HCl, pH 9.0. Fractions from the column were analysed for protease activity (using the Suc-AAPF-pNA assay at pH 9) and active fractions were analysed by SDS-PAGE. The fractions, where only one band was seen on the coomassie stained SDS-PAGE gel, were pooled and were used for further characterization.

Example 3

Characterization of the S1 Protease 2 from *Saccharopolyspora erythraea*

The Suc-AAPF-pNA assay was used for obtaining the pH-activity profile and the pH-stability profile (residual activity after 2 hours at indicated pH-values). For the pH-stability profile the protease was diluted 10× in the different assay buffers to reach the pH-values of these buffers and then incubated for 2 hours at 37° C. After incubation, the pH of the protease incubations was adjusted to the same pH-value by dilution in the pH 9.0 assay buffer. Residual activities were measured at pH 9.0 relative to a sample, which was kept at stable conditions (5° C., pH 9.0). The Protazyme AK assay was used for obtaining the temperature-activity profile at pH 7.0. The Suc-AAPX-pNA assay and ten different Suc-AAPX-pNA substrates were used for obtaining the P1-specificity of the enzymes at pH 9.0. The results are shown in tables 2-5 and FIGS. 1-4.

TABLE 2 pH-activity profile of at 37° C. as determined using the Suc-AAPF-pNA assay

| pH | S1 protease 2 from *Saccharopolyspora erythraea* | Protease 10R |
| --- | --- | --- |
| 2 | 0.00 | — |
| 3 | 0.00 | 0.00 |
| 4 | 0.01 | 0.02 |
| 5 | 0.06 | 0.07 |
| 6 | 0.25 | 0.21 |
| 7 | 0.56 | 0.44 |
| 8 | 0.86 | 0.67 |
| 9 | 1.00 | 0.88 |
| 10 | 0.95 | 1.00 |
| 11 | 0.84 | 0.93 |

Note:
activities are relative to the optimal pH for the enzyme.

TABLE 3 pH-stability profile (residual activity after 2 hours at 37° C.) as determined using the Suc-AAPF-pNA assay

| pH | S1 protease 2 from *Saccharopolyspora erythraea* | Protease 10R |
| --- | --- | --- |
| 2 | 0.04 | 0.78 |
| 3 | 0.21 | 1.03 |
| 4 | 0.93 | 0.99 |
| 5 | 1.01 | 1.00 |
| 6 | 0.98 | 1.03 |
| 7 | 0.98 | 1.01 |
| 8 | 0.96 | 0.98 |
| 9 | 0.94 | 0.99 |
| 10 | 0.88 | 0.99 |
| 11 | 0.22 | 0.86 |

TABLE 3-continued pH-stability profile (residual activity after 2 hours at 37° C.) as determined using the Suc-AAPF-pNA assay

| pH | S1 protease 2 from Saccharopolyspora erythraea | Protease 10R |
|---|---|---|
| After 2 hours at 5° C. | 1.00 (at pH 9) | 1.00 (at pH 9) |

Note:
activities are residual activities relative to a sample, which was kept at stable conditions (5° C., pH 9.0).

TABLE 4

Temperature activity profile as determined using the Protazyme AK assay

| Temp (° C.) | S1 protease 2 from Saccharopolyspora erythraea (pH 7) | Protease 10R (pH 6.5) |
|---|---|---|
| 15 | 0.12 | 0.01 |
| 25 | 0.18 | 0.02 |
| 37 | 0.45 | 0.06 |
| 50 | 0.81 | 0.13 |
| 60 | 1.00 | 0.35 |
| 70 | 0.33 | 0.96 |
| 80 | — | 1.00 |
| 90 | — | 0.18 |

Note:
activities are relative to the optimal temperature at pH 7.0 or 6.5 for the enzyme.

TABLE 5

P1-specificity on 10 Suc-AAPX-pNA substrates at 25° C. as determined using the Suc-AAPX-pNA assay

| Suc-AAPX-pNA | S1 protease 2 from Saccharopolyspora erythraea (pH 9) | Protease 10R (pH 9) |
|---|---|---|
| Suc-AAPA-pNA | 0.05 | 0.13 |
| Suc-AAPR-pNA | 0.11 | 0.09 |
| Suc-AAPD-pNA | 0.00 | 0.00 |
| Suc-AAPI-pNA | 0.00 | 0.00 |
| Suc-AAPM-pNA | 0.47 | 0.78 |
| Suc-AAPV-pNA | 0.00 | 0.01 |
| Suc-AAPL-pNA | 0.22 | 0.18 |
| Suc-AAPE-pNA | 0.00 | 0.00 |
| Suc-AAPK-pNA | 0.08 | 0.08 |
| Suc-AAPF-pNA | 1.00 | 1.00 |

Note:
activities are relative to the best substrate (Suc-AAPF-pNA) for the enzyme.

Other Characteristics for the S1 Protease 2 from *Saccharopolyspora erythraea*

Inhibitors: PMSF and CI-2A.

Determination of the N-terminal sequence by EDMAN degradation was: ADVIGGD.

The relative molecular weight as determined by SDS-PAGE was approx. $M_r$=21 kDa.

The molecular weight determined by intact molecular weight analysis was 18379.4 Da.

The mature sequence (from MS data, EDMAN degradation data and DNA sequence): ADVIGG-DAYYIGSGSRCSVGFSVQGGFVTAGHCGNQGDST-SQPSGTFEGSSFPGNDYGWVRTA SGENPVPLVN-DYQGGTVGVAGSSEAAEGASICRSGSTTGWHCG-TVEAKNQTVRYPQGTVEGLT RTNVCAE-PGDSGGSWLSGDQAQGVTSGGSGDCTSGGTTY-FQPVNEILQAYGLTLLTQ The calculated molecular weight from this mature sequence was 18379.6 Da.

Example 4

Soybean-Maize Meal Activity Assay

An end-point assay using soybean-maize meal as substrate was used for obtaining the pH activity profile of the proteases at pH 3-7.

Substrate: Soybean meal-maize meal mixed in a 30:70 ratio.

Assay buffers: 9 buffers containing 100 mM succinic acid, 100 mM HEPES, 100 mM CHES, 100 mM CAPS, 1 mM CaCl2, 150 mM KCl, 0.01% Triton X-100 were prepared and adjusted using HCl or NaOH to a pH value such that after soybean-maize meal substrate (1 g) had been mixed with assay buffer (10 mL) to give a slurry, the final pH of the slurry was one of the following pH's: 3.0, 4.0, 5.0, 6.0, 7.0, 8.0, 9.0, 10.0 and 11.0.

Substrate slurry (2 mL) was mixed for 30 min before protease addition and incubation for 3 hours at 40° C. (500 rpm). Protease (200 mg enzyme protein/kg dry matter) was dissolved in 100 µl 100 mM sodium acetate buffer (9.565 g/L NaOAc, 1.75 g/L acetic acid, 5 mM $CaCl_2$, 0.01% BSA, 0.01% Tween20, pH 6.0) and added. Samples were centrifuged (10 min, 4000 rpm, 0° C.) and the supernatants collected for analysis using the o-Phthaldialdehyde (OPA) assay.

The results are shown in Table 6 below and FIG. 5. The proteolytic activity of the S1 protease 2 from *Saccharopolyspora erythraea* on soybean-maize meal increases with increasing pH from pH 3 to pH 7. While the S1 protease 2 from *Saccharopolyspora erythraea* is as active as Protease 10R at pH 6-7, it shows somewhat higher activity at pH 3-5 indicating that the S1 protease 2 from *Saccharopolyspora erythraea* might have the potential to be more efficient at hydrolyzing protein along the entire gastro-intestinal tract of monogastric animals.

TABLE 6

Protease activity ($OD_{340}$ × dilution factor) on soybean-maize meal at pH 3.0 to 7.0 at 40° C.

| | S1 protease 2 from Saccharopolyspora erythraea | | Protease 10R | |
|---|---|---|---|---|
| pH | Average | Standard deviation | Average | Standard deviation |
| 3.0 | 0.36 | 0.01 | 0.22 | 0.06 |
| 4.0 | 0.54 | 0.03 | 0.30 | 0.10 |
| 5.0 | 0.87 | 0.01 | 0.71 | 0.01 |
| 6.0 | 1.76 | 0.05 | 1.81 | 0.14 |
| 7.0 | 2.90 | 0.02 | 2.92 | 0.11 |

Figure 5:
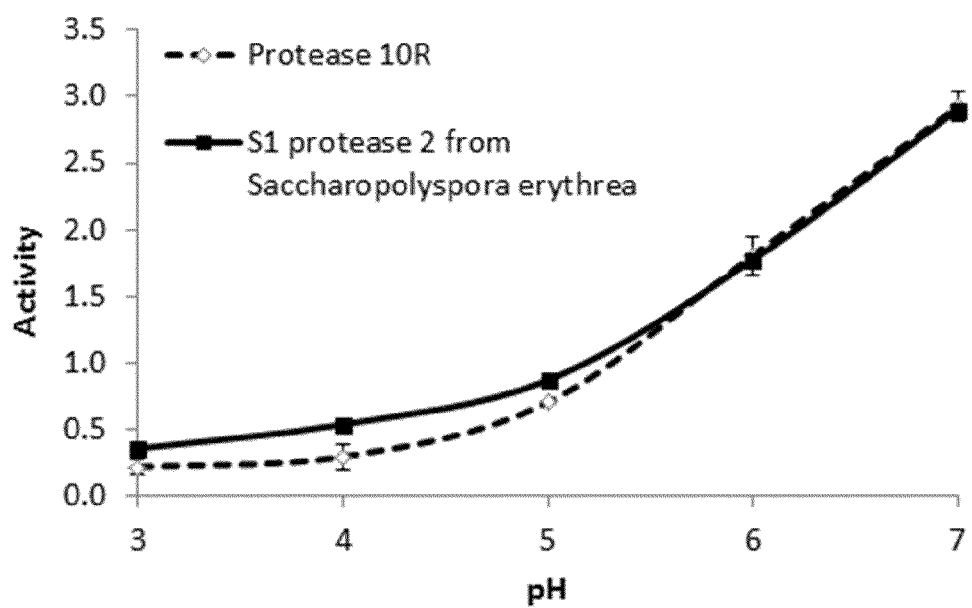
FIG. 5 shows the activity ($OD_{340}$×dilution factor) on soybean-maize meal of the S1 protease 2 as isolated from *Saccharopolyspora erythraea* compared to protease 10R.

FIG. 5 shows the activity ($OD_{340}$×dilution factor) on soybean-maize meal of S1 protease 2 from *Saccharopolyspora erythraea* compared to the 10R protease.

Example 5

Thermostability

An aliquot of the protein sample of protease (purified as described in Example 2) is either desalted or buffer-changed into 20 mM Na-acetate, pH 4.0 using a prepacked PD-10 column or dialysed against 2×500 ml 20 mM Na-acetate, pH 4.0 at 4° C. in a 2-3 h step followed by an overnight step. The sample is 0.45 µm filtered and diluted with buffer to approx. 2 A280 units. The dialysis buffer is used as reference in Differential Scanning calorimetry (DSC). The samples are degassed using vacuum suction and stirring for approx. 10 minutes.

A DSC scan is performed on a MicroCal VP-DSC at a constant scan rate of 1.5° C./min from 20-90° C. Data-handling is performed using the MicroCal Origin software (version 4.10), and the denaturation temperature, $T_d$ (also called the melting temperature, $T_m$) is defined as the temperature at the apex of the peak in the thermogram.

Example 6

Steam Stability

Residual activity of the protease after steam treatment may be evaluated using the following assay.

In these experiments a modified set-up is used whereby the steam is provided from a steam generator and led into the box. The samples placed on a plate are inserted into the box through a drawer when the temperature has reached ca. 93-94° C. Upon the insertion of the samples the temperature drops 4° C. Incubation is performed for 30 seconds while the temperature remains approximately constant at 90° C. Thereafter the plate is quickly removed from the box, the samples placed on ice, re-suspended and evaluated with respect to protease activity using the Suc-AAPF-pNA or o-Phthaldialdehyde (OPA) assay. Each enzyme sample is compared to a similar sample that had not been steam treated in order to calculate residual activity.

Example 7

Pelleting Stability Tests

The enzyme granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with palm oil and calcium carbonate in a manner as described in U.S. Pat. No. 4,106,991, Example 22.

Approximately 50 g enzyme granulate is pre-mixed with 10 kg feed for 10 minutes in a small horizontal mixer. This premix is mixed with 90 kg feed for 10 minutes in a larger horizontal mixer. From the mixer the feed is led to the conditioner (a cascade mixer with steam injection) at a rate of approximately 300 kg/hour. The conditioner heats up the feed to 95° C. (measured at the outlet) by injecting steam. The residence time in the conditioner is 30 seconds. From the conditioner the feed is led to a Simon Heesen press equipped with 3.0×35 mm horizontal die and pressed to pellets with a length of around 15 mm. After the press the pellets are placed in an air cooler and cooled for 15 minutes.

The protease activity is measured using the Suc-AAPF-pNA assay prior to pelleting and in the feed pellets after pelleting. Pelleting stability is determined by comparing the protease activity in pelleted feed relative to the activity in non-pelleted feed.

What is claimed is:

1. A variant polypeptide having protease activity and at least 85% sequence identity and less than 100% sequence identity to the polypeptide of SEQ ID NO: 5 and comprising at least one substitution, deletion, and/or insertion at one or more positions.

2. The variant polypeptide of claim 1, which has at least 90% sequence identity to the polypeptide of SEQ ID NO: 5.

3. The variant polypeptide of claim 1, which has at least 95% sequence identity to the polypeptide of SEQ ID NO: 5.

4. The variant polypeptide of claim 1, which has at least 97% sequence identity to the polypeptide of SEQ ID NO: 5.

5. An animal feed additive comprising:
   (a) at least one polypeptide having protease activity, wherein the polypeptide is selected from the group consisting of
      (i) a polypeptide having at least 85% sequence identity to SEQ ID NO: 5;
      (ii) a polypeptide encoded by a polynucleotide that hybridizes under high stringency conditions with:
         (i) the mature polypeptide coding sequence of SEQ ID NO: 1;
         (ii) the mature polypeptide coding sequence of SEQ ID NO: 3; and/or
         (iii) the full-length complementary strand of (i) or (ii)
      wherein the high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours, followed by washing three times each for 15 minutes using 2×SSC, 0.2% SDS at 65° C.;
      (iii) a polypeptide encoded by a polynucleotide having at least 85% sequence identity to the mature polypeptide coding sequence of SEQ ID NO: 1 and/or SEQ ID NO: 3;
      (iv) a variant of the polypeptide of SEQ ID NO: 5 having at least 85% sequence identity to the polypeptide of SEQ ID NO: 5 comprising a substitution, deletion, and/or insertion at one or more positions; and
      (v) a fragment of the polypeptide of SEQ ID NO: 5, which has protease activity; and
   (b) at least one fat-soluble vitamin, at least one water-soluble vitamin, and/or at least one trace mineral.

6. The animal feed additive of claim 5, which further comprises one or more amylases; galactanases; alpha-galactosidases; beta-glucanases, phospholipases, phytases; proteases; xylanases; or a mixture thereof.

7. The animal feed additive of claim 5, wherein the polypeptide has at least 90% sequence identity to the polypeptide of SEQ ID NO: 5.

8. The animal feed additive of claim 5, wherein the polypeptide has at least 95% sequence identity to the polypeptide of SEQ ID NO: 5.

9. The animal feed additive of claim 5, wherein the polypeptide is encoded by a polynucleotide having at least 90% sequence identity to the mature polypeptide coding sequence of SEQ ID NO: 1 and/or SEQ ID NO: 3.

10. The animal feed additive of claim 5, wherein the polypeptide is encoded by a polynucleotide having at least 95% sequence identity to the mature polypeptide coding sequence of SEQ ID NO: 1 and/or SEQ ID NO: 3.

11. An animal feed comprising an animal feed additive of claim 5.

12. The animal feed of claim 11 having a crude protein content of 50 to 800 g/kg.

13. A method for degrading a protein, comprising adding at least one polypeptide of claim 1 to at least one protein or protein source.

14. The method of claim 13, wherein the protein source comprises soybean.

15. An isolated polynucleotide encoding a variant polypeptide of claim 1 provided that the polynucleotide is not 100% identical to SEQ ID NO: 1 or the mature polypeptide coding part thereof.

16. A nucleic acid construct or expression vector comprising a polynucleotide of claim 15, wherein the polynucleotide is operably linked to one or more control sequences that direct the production of the variant polypeptide in a recombinant host cell.

17. A recombinant host cell comprising the nucleic acid construct or expression vector of claim 16.

18. A method of producing a variant polypeptide having protease activity, comprising:
(a) cultivating the recombinant host cell of claim 17 under conditions conducive for production of the polypeptide; and
(b) recovering the polypeptide.

19. The method of claim 18, wherein the variant polypeptide has at least 90% sequence identity to the polypeptide of SEQ ID NO: 5.

20. The method of claim 18, wherein the variant polypeptide has at least 95% sequence identity to the polypeptide of SEQ ID NO: 5.

* * * * *